(12) United States Patent
Shiki

(10) Patent No.: US 7,044,913 B2
(45) Date of Patent: May 16, 2006

(54) ULTRASONIC DIAGNOSIS APPARATUS

(75) Inventor: Eiichi Shiki, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/170,573

(22) Filed: Jun. 14, 2002

(65) Prior Publication Data

US 2003/0125624 A1    Jul. 3, 2003

(30) Foreign Application Priority Data

Jun. 15, 2001    (JP) .......................... P.2001-182535

(51) Int. Cl.
*A61B 8/02*    (2006.01)

(52) U.S. Cl. ...................... 600/454; 600/437; 600/440; 600/441; 600/443; 600/453; 600/465; 600/468

(58) Field of Classification Search ......... 600/437–472
See application file for complete search history.

(56) References Cited

U.S. PATENT DOCUMENTS

| | | | |
|---|---|---|---|
| 5,513,640 A * | 5/1996 | Yamazaki et al. | 600/455 |
| 5,628,321 A * | 5/1997 | Scheib et al. | 600/453 |
| 5,868,676 A * | 2/1999 | McCabe et al. | 600/454 |
| 5,899,864 A * | 5/1999 | Arenson et al. | 600/455 |
| 6,485,424 B1 * | 11/2002 | Suzuki | 600/458 |

FOREIGN PATENT DOCUMENTS

| | | |
|---|---|---|
| JP | 2-161934 | 6/1990 |
| JP | 5-95947 | 4/1993 |
| JP | 5-261100 | 10/1993 |
| JP | 5-317311 | 12/1993 |
| JP | 2000-152935 | 6/2000 |

* cited by examiner

*Primary Examiner*—Ali Imam
*Assistant Examiner*—William Jung
(74) *Attorney, Agent, or Firm*—Oblon, Spivak, McClelland, Maier & Neustadt, P.C.

(57) ABSTRACT

An ultrasonic diagnosis apparatus comprises an ultrasound probe, a transmitter (including a transmitting pulse generator and a transmitting beamformer), a receiver (including a preamplifier and a receiving beamformer), a CFM processor (including a moving-element signal extractor and a velocity corrector), a tomographic image processor, and a display unit. The apparatus scans a desired section of a subject by transmitting and receiving an ultrasound pulse to and from the subject, and displays images obtained by the scanning. The velocity corrector comprises a pulsation-characterizing-velocity (velocities of a moving element) calculator, a representative velocity (reference velocity) calculator, and a corrector to correct the velocities of the moving element based on the standard velocity. The corrected velocity data is visualized on display unit. The ultrasonic diagnosis apparatus makes it possible to display the pulsatility of blood vessels in an easier and useful way.

21 Claims, 27 Drawing Sheets

OVERHEAD VIEW OF (a)

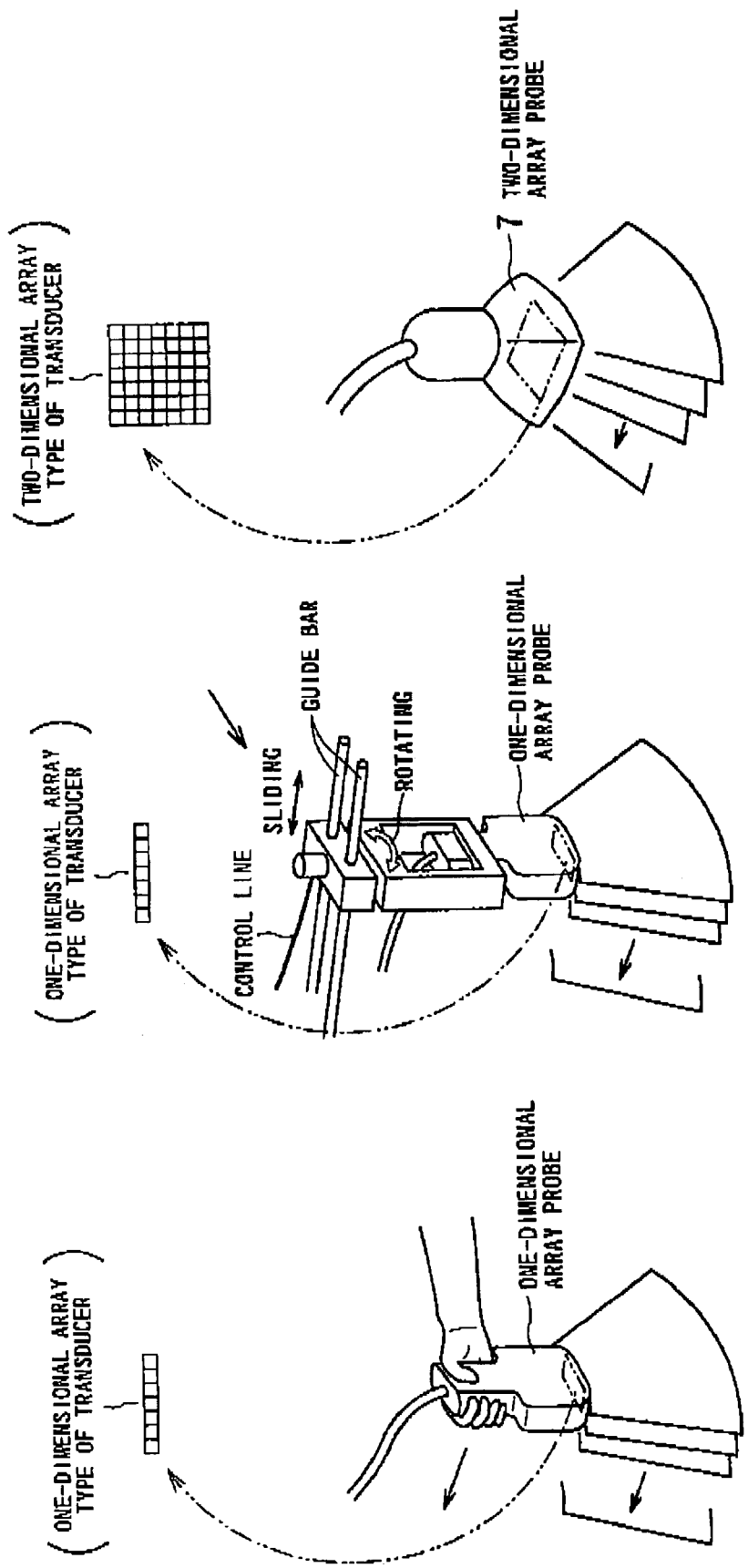

FIG. 23
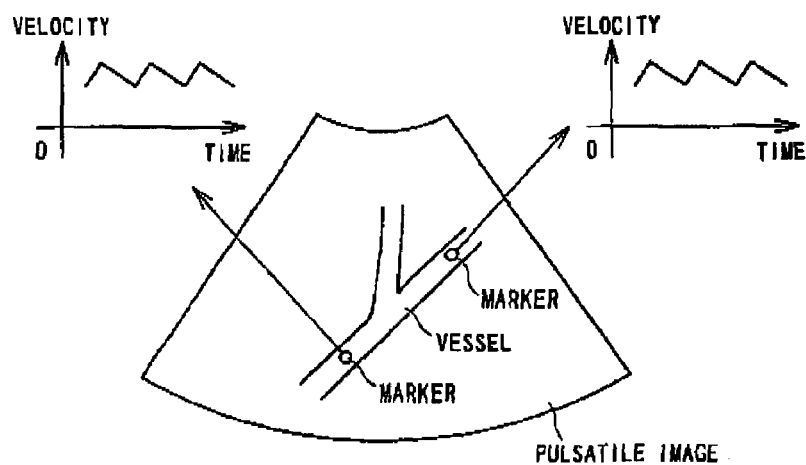
FIG. 24
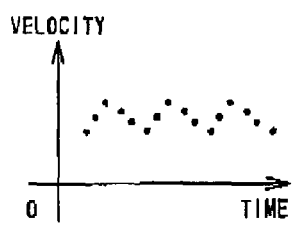 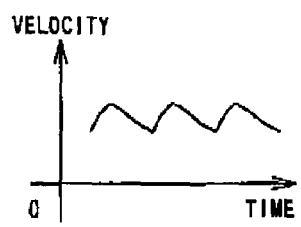 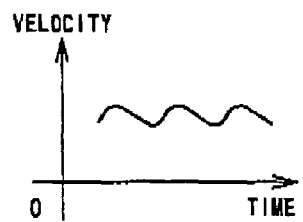
FIG. 25(a)    FIG. 25(b)    FIG. 25(c)

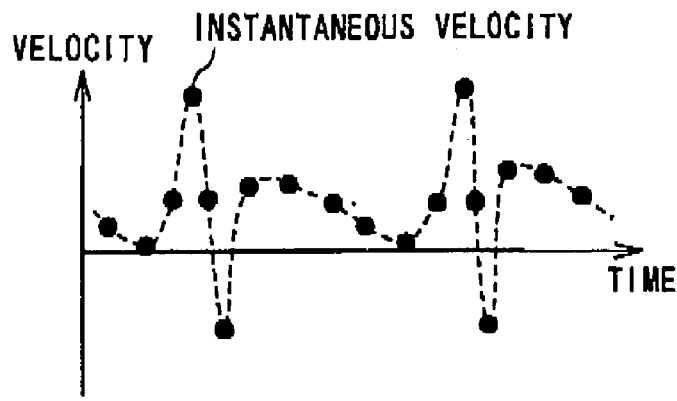

(TEMPORAL CHANGE IN VELOCITY AT ANY PIXEL ON COLOR MAP)

⇩ ABSOLUTE VALUE OF INSTANTANEOUS VELOCITY

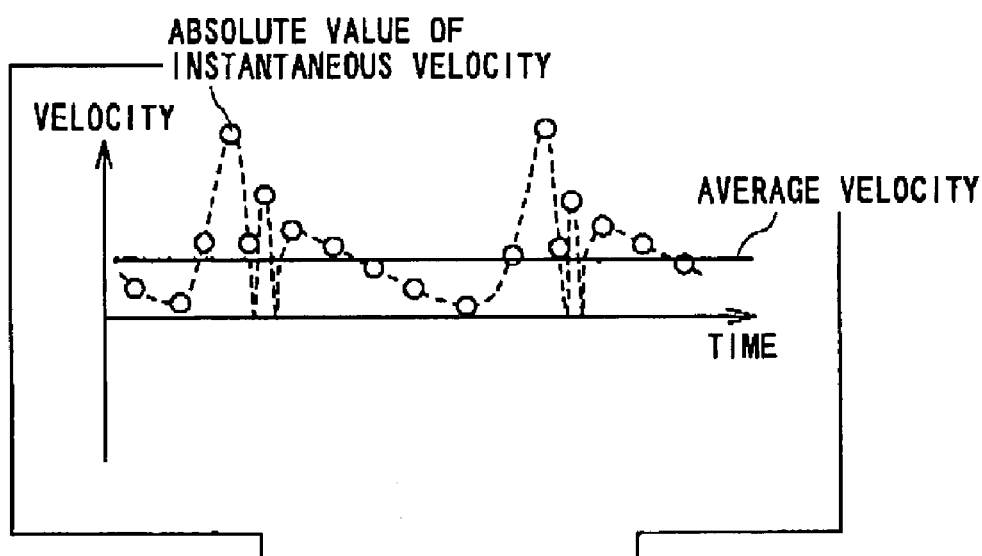

$$\left(\begin{array}{c}\text{CORRECTED}\\\text{VELOCITY}\end{array}\right) = \left(\begin{array}{c}\text{ABSOLUTE VALUE}\\\text{OF INSTANTANEOUS}\\\text{VELOCITY}\end{array}\right) \Big/ \left(\begin{array}{c}\text{MEAN ABSOLUTE}\\\text{VALUE OF VELOCITY}\\\text{PER HEART RATE PERIOD}\end{array}\right)$$

FIG. 26

ULTRASONIC DIAGNOSIS APPARATUS

BACKGROUND OF THE INVENTION

1. Field of the Invention

The present invention relates to an ultrasonic diagnosis apparatus capable of not only effectively displaying dynamic states of flow of blood in a subject to be examined, particularly, pulsation of the flow of blood, but also three-dimensionally displaying pulsatile flows of blood in the subject.

2. Description of Related Art

An ultrasonic diagnosis apparatus has normally various types of displaying images, as has been widely known, which can be used for diagnosis on ultrasound images. Such types of displaying images include a CFM (Color Flow Mapping) mode used for displaying blood flow images, as well as tomographic image modes, such as a B-mode, used for displaying tomographic images.

Among these modes, the CFM mode is prepared for displaying two-dimensional blood flow information in real time. In this mode, generally, flows of blood approaching to the ultrasound probe are displayed in red on a monitor, while flows of blood going away from the probe are displayed in blue on the monitor, so that information about blood flow is visually distinguishable.

The following describes the principle and an outline of process for displaying information in relation to blood flow on the CFM mode. As conventionally well known, an ultrasonic diagnosis apparatus obtains echo signals sequentially in time by performing ultrasound scanning at each location (direction) in a subject to be examined a plurality of times (N-times). Then, from the echo signals obtained sequentially in time, the apparatus detects information in relation to velocity and/or scattering power of blood flow at a desired depth in the scanned region on the basis of the Doppler technique. That is, scanning the same location in the subject at predetermined intervals provides Doppler signals expressed as a quantity of phase shift per unit time of signals (blood flow signals) reflected from blood cells. The Doppler signals thus obtained are converted to data of velocity and/or scattering power of blood flow.

More precisely, applying quadrature phase detection to the echo signal at each time of ultrasound scanning with the use of mixers and LPFs (Low Pass Filters) provides an I (In-Phase) signal and a Q (Quadrature-Phase) signal, both of which are extracted as Doppler signals.

The extracted Doppler signals contain by mixture a reflected wave signal from objects in motion (moving elements), such as blood cells, and a second reflected wave signal (called Clatter Signals) from almost non-moving fixed objects, such as the blood vessel wall and organ parenchyma. Of these wave signals, the reflected wave signal from the objects in motion contains a Doppler shift. In contrast, the reflected signal from the fixed objects hardly contains a Doppler shift, and is so high in its intensity that the signal is a dominant in the detected signal.

Therefore, clatter components representing the reflected wave from the fixed objects are eliminated through an MTI (Moving Target Indicator) filter by taking advantage of a difference in the quantity of Doppler shift, a blood flow Doppler signal can be efficiently extracted. Then, through analysis of the frequency of this blood flow Doppler signal, i.e., N-pieces of Doppler data composed of $x_i$ (I signal) and $y_i$ (Q signal) at each depth (where i=1, 2, . . . , N), a mean derived from the spectra (i.e., a Doppler frequency), a dispersion of the spectra, or a reflection intensity (power) from blood cells can be calculated.

For this frequency analysis, an autocorrelation function is normally used. A frequency analysis technique that uses the autocorrelation function will now be exemplified. As above described, the blood flow Doppler signal obtained by eliminating its clatter components at the MTI filter is expressed by a complex number $z_i$ composed of Doppler data $x_i$ and $y_i$, each is N-pieces in number, and expressed by the equation of:

$$z_i = x_i + jy_i \quad (1)$$
$$= a_i \cdot \exp[j\{2\pi f_d T_{rm}(i-1) + \phi\}],$$
$$(i = 1, 2, \ldots, N)$$

where $a_i$ is an amplitude, $f_d$ is a Doppler frequency, $T_{rm}$ is intervals of transmission of ultrasound pulses along an arbitrary raster direction, and $\phi$ is an initial phase respectively. For the sake of explanatory convenience, it is assumed that the Doppler frequency $f_d$ is constant over the N-pieces Doppler data, still maintaining the generality of the equation.

According to the above equation (1), the phase rotation of the complex number $z_i$ per unit time provides a Doppler frequency $f_d$. Where a mean complex autocorrelation function for the N-piece Doppler data is:

$$Z = X + jY = A \cdot \exp[j\eta], \quad (2)$$

the following equation can be obtained:

$$Z = (N-1)^{-1} \sum_{i=1}^{N-1} Z_i * Z_{i+1} \quad (3)$$
$$= (N-1)^{-1} \Sigma a_i \cdot a_{i+1} \exp[j\{2\pi f_d T_{rm}\}].$$

The Doppler frequency $f_d$ is therefore expressed as:

$$f_d = (2\pi)T_{rm}^{-1} \tan^{-1}(Y/X), \quad (4)$$
$$X = \Sigma(x_i x_{i+1} + y_i y_{i+1})$$
$$Y = \Sigma(x_i x_{i+1} - y_i y_{i+1})$$

By employing this Doppler frequency $f_d$, the equation of:

$$V_d = f_d \cdot c/(2f_M \cos\theta) \quad (5)$$

can be obtained, so that a Doppler velocity $V_d$ is converted using this equation (5). In this equation (5), c, $f_M$ and $\theta$ indicate a sound velocity, the frequency of a reference signal at the mixers, and an angle formed between an ultrasound beam and each blood flow (hereinafter referred to as a "Doppler angle"), respectively.

In the case of a CFM mode, due to difficulty in obtaining Doppler angles at each position in the space of an image, which vary position by position therein, the correction of Doppler angles is omitted from the computation on the foregoing equation (5). In other words, in the CFM mode, the Doppler velocity $V_d$ can be calculated based on the equation of:

$$V_d = f_d \cdot c/(2f_M) \quad (6),$$

and is subjected to display in colors. Consequently, where the Doppler angle is larger, a calculated value becomes smaller than its original correct velocity, with the result that the Doppler velocity $V_d$ is subject to display based on color intensities representing slower velocity states (this is called "angle dependency").

Blood flow velocities obtained as described above are two-dimensionally displayed on a monitor, normally, together with a B-mode topographic image displayed as a background.

In recent years, three-dimensional image display in ultrasonic diagnosis apparatuses has been extensively researched and developed, and it has been possible to three-dimensionally display a power image of blood flow. For such a display, for acquiring three-dimensional data, a hand scanning technique by which an electronic scanning probe with one-dimensionally arrayed transducers is used, for example.

To operate this hand scanning, while being electronically scanned in the direction along the transducer array, an operator moves his or her hand holding the probe so that the probe is moved to orthogonal directions to the transducer array direction.

However, the display on the current CFM mode has encountered the following problems.

First, in recent years, as various types of diagnostic methods have been advanced, there are demands for a display technique that allows a user to identify a blood vessel as an artery, portal vein, or vein in a steadier and easier manner. In particular, to identify a blood vessel as described above by using an ultrasound wave, it is considered effective to observe pulsation appearing in blood flow.

As one conventional examination method for examining pulsatility of this kind of blood vessel, one display method called "pulsatility index (PI)" has been known. The PI is an index that quantifies the extent of change in a blood flow velocity per heartbeat. Since peripheral circulatory resistance in blood vessels is reflected in the PI, it is deemed effective for early detection of dysgenesis of fetuses in the obstetrical department and for differential diagnosis of tumor in the abdominal part (refer to, for example, a Japanese Patent Laid-open (KOKAI) Publication No. H05-317311).

Other conventional examination methods are provided to examine the pulsatility of blood vessels, for example. One method is to display an acceleration of blood flow calculated from two frames of blood flow velocity data which are adjacent in time and stored in a frame memory (Japanese Patent Publication No.2768959). Using this method, information about the pulsation of acceleration of a blood flow can be added on two-dimensional color flow map information or three-dimensional display information based on the CFM mode. Another method is proposed by an ultrasound imaging method and apparatus that is able to display an image of intensity of the pulsation appearing in the moving velocity of an echo source (Japanese Patent Application Laid-open (KOKAI) Publication No.2000-152935). This method comprises the steps of detecting a moving velocity of an echo source based on Doppler shifts of received echoes, detecting intensities of the pulsation appearing in the moving velocity calculated on moving velocities at the current and past temporal phases, and producing an image indicative of the detected intensities of the pulsation. Those methods have not, however, reached a level of practical use yet.

Besides, the present CFM mode has a difficulty to clearly display the pulsatility of blood flow in displaying its power. It is considered that displaying the velocities of blood flow still provides distinguishable observation with respect to the pulsatility. In other words, temporal changes in the colors indicative of velocities shows that there is pulsatility in a blood flow to be observed, while no temporal changes in such colors shows that, there is no pulsatility in the blood flow. However, there are many cases that make it difficult a clear discrimination of blood flows even if carefully watched, thereby still lacking practically. Whichever of the display techniques are chosen, a more convenient display technique is required to provide the pulsatility of blood flow.

Especially in the case of peripheral blood vessels, their blood flow velocities are relatively lower, amounts of changes in the velocities showing the pulsatility are also small, even in arteries. It is therefore considerably difficult to distinguish an artery from a vein or vise versa on a displayed image. In addition, displaying the velocity has the problem of the angle dependency if the Doppler angle is larger, as described before, resulting in that detected velocities are smaller than their original correct velocities. It is therefore very difficult to detect the pulsatility, like the situation in peripheral blood vessels.

On the other hand, in the foregoing three-dimensional display, a further advanced display rather than the simple display of blood vessels is demanded. Such advanced display techniques include a display technique that has the capability of classifying the types of blood vessels, such as artery, portal vein, or vein. For this purpose, it is also considered advantageous that such display involves pulsatile flows of blood, which requires an ultrasonic diagnosis apparatus that is able to three-dimensionally display the pulsatility.

SUMMARY OF THE INVENTION

The present invention has been made in consideration with the above problems, and an object of the present invention is to provide an ultrasonic diagnosis apparatus that is able to effectively display the pulsatility of blood vessel in a simple and easy way.

A further object of the present invention is to provide an ultrasonic diagnosis apparatus suitable for displaying the pulsatility of blood vessel in a three-dimensional manner.

In order to achieve the objects, the ultrasonic diagnosis apparatus according to the present invention is characteristic of having, as basic constituents, scanning means for scanning a subject to be examined while transmitting and receiving an ultrasound pulse to and from the subject; means for obtaining in sequence a plurality of velocities of a moving element within the subject based on reception signals acquired by the scanning performed by the scanning means; processing means for computing a reference velocity based on the plurality of velocities obtained from during a predetermined period of time and correcting each of the velocities of the moving element using the reference velocity so that data of the corrected velocities is obtained; and displaying means for displaying the data so that the data is updated a plurality of times during the predetermined period of time.

In the present invention, it is possible that the processing means has extracting means for extracting a signal of the moving element from the reception means.

In the present invention, by way of example, an instantaneous velocity can be adopted as a "velocity of a moving element" (that is, a velocity indicating a characteristic of the pulsation) within a subject to be examined. In addition, to a "reference velocity" (that is, a representative velocity), assigned is at least one selected from 1) a mean of velocities acquired during a predetermined period of time or an absolute value of the mean thereof, 2) a mean of absolute values of velocities acquired during a predetermined period of time, 3) an RMS (Root Mean Squire Value) value of velocities acquired during a predetermined period of time, 4) a value or an absolute value thereof, which is calculated by applying any one of an FIR (Finite Impulse Response) filter, IIR (Infinite Impulse Response) filer, and a non-linear filter to velocities acquired during a predetermined period of time or absolute values of the velocities, and 5) a vectorial mean of velocities acquired from a predetermined period of time or an absolute value of the mean. Preferably, the predetermined period of time is one heartbeat of the subject, a period of time corresponding to one heartbeat, or a period of time during which the effects identical to that in one heartbeat are provided.

In the present invention, the processing means comprises at least one of 1) means for dividing the velocities of the moving element by the reference velocity, and 2) means for converting the velocities of the moving element to values relative to the reference velocity.

Preferably, the processing means according to the present invention has correction means for correcting the aliasing of the velocities. Further, the present invention may have moderation means for moderating temporal changes in the data obtained by the processing means. It is preferred that the scanning means according to the present invention has scanning means for scanning one section of the subject at the number of frames larger than a value indicated by an inverse number of a period of time corresponding to an ejection period of cardiac pulsation.

In the present invention, the display means is configured to display a two-dimensional image based on the data obtained by the processing means.

An ultrasonic diagnosis apparatus according to another aspect of the present invention comprises scanning means for three-dimensionally scanning one section of a subject to be examined a plurality of times corresponding to one heartbeat while transmitting and receiving an ultrasound pulse to and from the subject; means for obtaining in sequence velocities of a moving element within the subject based on reception signals obtained three-dimensionally by the scanning means; processing means for computing a reference velocity based on the plurality of velocities obtained from during a predetermined period of time and correcting each of the velocities of the moving element using the reference velocity so that data of the corrected velocities is obtained; and displaying means for displaying at least a three-dimensional image based on the data so that the image is updated a plurality of times during the predetermined period of time.

In the present invention, in the case that the three-dimensional scan is carried, it is preferred that the scanning means is configured to three-dimensionally scan the subject through an electrical scan by means of a two-dimensional array type of transducer. It is also preferred that the velocities of the moving element are set to a maximum velocity during a predetermined period of time. In the case of displaying a three-dimensional image of information about the pulsatility of the subject in the present invention, it is preferred that such information is unchangeable over cardiac time phases of the subject.

As another aspect of the present invention, the ultrasonic diagnosis apparatus further comprises means for obtaining a tomographic image of the section of the subject, and the display means is able to display on the same monitor the tomographic image and the image of data obtained by the processing means. In this case, it is more effective if the display means is configured to display on the tomographic image the image of data obtained by the processing means in a superposition manner. Furthermore, for three-dimensional display in the present invention, the tomographic image may be a three-dimensional image. In the present invention, it is preferable that an image based on the data obtained by the processing means is depicted in colors.

As another aspect of the present invention, it is possible to display pieces of information formed by combining the data obtained by the processing means and power information of scattering echoes from the moving element within the subject. In this configuration, the display can be more effective in cases where the ultrasonic diagnosis apparatus has means for displaying a color bar mapped not only by a hue indicative of a lower velocity when a magnitude of the data obtained by the processing means is nearly equal to or less than the representative velocity but also by other hues indicative of higher velocities as the magnitude of the data obtained by the processing means becomes larger than a value nearly equal to the representative velocity.

As another aspect of the present invention, it is preferred that the image of the data obtained by the processing means and an information of power information of scattering echoes from the moving element within the subject are displayed by mixture. It is also possible to display by mixture an image of the power information and an image of information formed by combining the data obtained by the processing means and the power information. In this case, it is desired that both of a color bar for the data obtained by the processing means and another color bar for the power information are displayed together. It may also be possible to display together both of a color bar indicative of a combination of the data obtained by the processing means and the power information and another color bar for the power information. A more effective example is that setting means is used to set an upper limit and a lower limit on the color bar for the data obtained by the processing means, and/or at least one of an upper limit, a lower limit, and an aliasing velocity on the color bar for the data obtained by the processing means is displayed.

As described above, in the ultrasonic diagnosis apparatus according to the present invention, the scanning means operates to scan a section to be imaged of a subject through a plurality of times of transmission and reception of an ultrasound pulse along the same raster direction of the raster directions required for the scanning within the subject. The processing means thus operates as follows. A tissue signal is removed from a reception signal obtained by the scanning conducted by the scanning means, at every sample point of the section that has been scanned, so that a blood flow signal is extracted. Based on this blood flow signal, velocities of a moving element (i.e., velocities which are characteristic of the pulsation) and a reference velocity (i.e., a representative velocity) are figured out. And the velocities of the moving element are corrected using the reference velocity. Therefore, under the operations of the display means, data thus-obtained at individual sample points is depicted as for example a two-dimensional or three-dimensional image.

Accordingly, the velocities of a moving element are corrected based on the reference velocity, which makes it possible that the pulsatility of slower-speed blood flows, such as flows passing the peripheral blood vessels, is depicted distinctively. Further, a Doppler angle dependency is also removed, with the result that the pulsatility of blood flows is clearly provided even if a Doppler angle becomes larger. Because the data that has been subjected to the correction is used for the display, the pulsatility can be depicted easily and more effectively, compared to the conventional CFM power images and velocity images. It is therefore possible to upgrade visibility for the artery, portal vein and vein, thus contributing to an improved diagnostic performance.

In particular, provided that instantaneous velocities are used as the velocities of a moving element, the display of the pulsatility becomes excellent, in which dynamic pulsatile changes are depicted in real time, with the visibility for the pulsatility enhanced. Suitable for the reference velocity are: a mean of instantaneous velocities acquired during a predetermined period of time or an absolute value of the mean thereof; a mean of absolute values of instantaneous velocities acquired during a predetermined period of time; an RMS (Root Mean Squire Value) value of instantaneous velocities acquired during a predetermined period of time; a value or an absolute value thereof, which is calculated by applying any one of an FIR (Finite Impulse Response) filter, IIR (Infinite Impulse Response) filer, and a non-linear filter to instantaneous velocities acquired during a predetermined period of time or absolute values of the instantaneous velocities; and a vectorial mean of instantaneous velocities acquired from a predetermined period of time or an absolute value of the mean.

In addition, preferably, the predetermined period of time is a period of one heartbeat or a period of time corresponding to one heartbeat. Alternatively, the predetermined period of time may be any other period of time selected to have the similar effects to the period of time of one heartbeat. The simplest and most useful technique for the correction is to use the division. Namely, utilizing the division allows the pulsatility of slower blood flows such as peripheral blood flows to be depicted clearly, and the problem resulting from the Doppler angle dependency can be removed. Moreover, by correcting the aliasing of velocities, the present invention is also applicable to faster velocities of moving bodies, thus making the application more effective.

In addition, in cases where it is felt that the real-time display of the pulsatility is hard to observe due to faster temporal changes thereof on the image, such temporal changes on the image can be moderated to raise the visibility.

Further, a specified section of the subject is scanned at the number of frames larger than a value indicated by an inverse number of a period of time corresponding to an ejection period of cardiac pulsation. This scanning makes sure that the ejection period is traced without failure, whereby the pulsatility can be depicted in a steadier manner and a diagnostic performance can be improved. The reason is as follows. The pulsation is caused by the pumping action of the heart and the ejection period of one cardiac cycle is characteristic of the pulsation. A blood flow speed at the vein and the portal vein is almost constant over one cardiac cycle, while a blood flow speed at the artery increases sharply and then decreases in the ejection period, and then gradually decreases until the next ejection period begins. It is therefore very significant to steadily track the ejection period for detecting the pulsatility.

For obtaining a three-dimensional image, the scanning means is operated to scan a subject in a three-dimensional manner, while the display means is operated to display a three-dimensional image based on the data obtained through the scanning. The three-dimensional scanning carried out by the scanning means requires a specified section of the subject to be scanned a plurality of times. This scanning is able to provide both of velocities of a moving element and a reference velocity at each section to be scanned, three-dimensional data that has been corrected, and a three-dimensional image according to the present invention.

In cases where such a three-dimensional image based on information about the pulsatility of a blood flow within a subject is displayed through the three-dimensional scanning, it is preferred that a specified section of the subject is scanned three-dimensionally a plurality of times. This manner will provide a three-dimensional image in which the pulsatility is depicted with higher accuracy, whereby such an image is able to contribute to an enhanced diagnostic performance.

In order to effectively implement the three-dimensional scan of the present invention, the most suitable technique is to use a two-dimensional array type of transducer to three-dimensionally scan a subject under an electrical staring scanning.

Furthermore, when a maximum velocity detected during a period of time is used as velocities of a moving element, a higher-pulsatility blood vessel, such as the artery, is always depicted in hues showing higher pulsatility, whilst a lower-pulsatility blood vessel, such as the portal vein and vein, is always depicted in hues showing lower pulsatility. Accordingly, images characteristic of the pulsatility, which are acquired at each of the cardiac time phases, can be obtained at any time. Hence, it is still preferable that such an image can be combined with the foregoing three-dimensional image, wherein two-dimensional pulsatile images, which become fundamental images for a three-dimensional image, can be acquired irrelevantly to changes in the cardiac time phase. Therefore, a three-dimensional pulsatile image can be constructed easily. In general, when information indicative of the pulsatility of a blood flow within a subject is acquired as information irrelevantly to changes in the cardiac time phase, a three-dimensional pulsatile image can be constructed easily.

In the case of displaying the foregoing two-dimensional and three-dimensional pulsatile images, means for acquiring a topographic image at a section of a subject can be provided as well. In such a construction, under the operations of the display means, both of the tomographic image and an image on the data obtained by the processing means can be depicted on the same monitor. This makes it easier to identify the position of a blood vessel to be observed, thus providing an image of highly improved visibility. Hence a further enhancement of a diagnostic performance is possible.

In particular, it is more effective when the display means operates to overlay, on the tomographic image, the image on the data obtained by the processing means. If performing the three-dimensional display, the tomographic image may be of a three-dimensional tomographic image, not being limited to a two-dimensional tomographic image. When the pulsatile image to be overlaid is depicted in colors, it is sure that the visibility will be upgraded more, being useful in observing the image. In this configuration, the data obtained by the processing means may be combined with scattering power detected from a moving element within a subject so that an image expressing the combination is depicted in colors. This display is able to largely raise a visual effect on the image.

As another feature, the reference velocity may be a mean of the velocities that have been detected. In such a construction, when magnitudes of the data obtained by the processing means are close to a representative velocity, the above mean is almost equal to a velocity detected at each of the cardiac time phases of both the vein and portal vein. In the case of the artery, however, the above mean is almost equal to a velocity detected at each of the cardiac time phases other than the ejection period. Considering to this fact, it is preferable to display a color bar mapped not only by a hue indicative of a lower velocity when magnitudes of the data obtained by the processing means are nearly equal to or less than a reference velocity but also by other hues indicative of higher velocities as the magnitude of the data obtained by the processing means becomes larger than a value nearly equal to the reference velocity. This display of the color bar will make it possible that the hues assigned to the pulsatility and non-pulsatility is distinctively distinguished one from the other, resulting in that the pulsatility can be distinguishably visualized with ease, thus contributing to a more improved diagnostic performance.

By the way, breathing, heartbeats, and/or others may cause an organ to move within a subject. If such a movement happens in connection with blood vessels, such as peripheral blood vessels or blood vessels whose Doppler angles are larger, it is conceivable that blood flow signals are obliged to stop detecting temporarily or depending on some particular cardiac time phases. In such a situation, a reference velocity cannot be determined, so that velocities of a moving element cannot be corrected. In other words, it is impossible to correct the velocities, but only the detection of velocities (accordingly, instantaneous blood flow signals) of a moving object is possible.

In such a situation, thought the data obtained by the processing means cannot be subjected the display of an image thereof (that is, an image indicative of the pulsatility), power display that represents the existence of a blood flow(s) is at least possible. Hence, the following display strategy can be given. Namely, in cases where velocities of a moving element have been corrected, the data obtained by the processing means is then subjected to displaying images thereof. By contrast, in cases where such velocities are no longer corrected, though blood flow signals have been detected, the corrected velocities are made to undergo the power display. In other words, an image on the data obtained by the processing means and a power image are displayed by mixture.

This mixing display technique enables the visualization of all the blood vessels that have been detected. To be specific, the pulsatility can be depicted toward blood vessels if the velocities of blood flowing therethrough have been corrected. In that case, the pulsatility can be visualized at higher vessel detectability, thus being able to largely improve a diagnostic performance. When coloring is applied to both of the pulsatile image and the power image, the visibility to the mixed image can be more raised. Alternatively, the depiction of a color image concerning information produced by combining the data obtained by the processing means and scattering power detected from a moving element within a subject may be applied to a region at which it has been possible to correct the velocities. This display technique will further raise a visual effect on the image.

In the above display mode, both of a color bar showing the pulsatility and another color bar showing the power should be put on the image. The former color bar will help a viewer distinguish the pulsatility from the other with ease. In addition, in cases where the depiction of a color image concerning information produced by combining the data obtained by the processing means and scattering power detected from a moving element within a subject is applied to a region at which it has been possible to correct the velocities, one color bar can be adopted such that hues showing the pulsatility are taken longitudinally and other hues showing the power are taken laterally, for instance. This two-dimensional color bar and the color bar for the power can both be placed on the same image(s).

In association with the display of the above color bars, upper and lower limits of the pulsatility can be put on the color bars. When such display of the limits is carried out, the relationship between the hues and degrees of the pulsatility is clearly specified, thus allowing an observer to easily recognize a degree of the pulsatility, thus contributing to an enhanced diagnostic performance. In addition, using means for setting values to the upper and lower limits on a color bar, an observer can give proper values to those limits. This will lead to a more effective display of the pulsatility, whereby an enhanced diagnostic performance can be expected. Additionally putting an aliasing velocity on a color bar allows a velocity range to be set adequately, which results in a steadier detection of the pulsatility, with the delectability improved.

As described above, according to one aspect of the present invention, corrected velocities of blood flow can be displayed two- or three-dimensionally to provide information about the pulsatility in a steadier way with the artery, vein, portal vein and others distinguished one from another. Accordingly the visibility toward blood flows is greatly raised, both of efficiency and accuracy of diagnostic examinations are upgraded, thus leading to an improved diagnostic performance.

Furthermore, as another aspect of the present invention, a three-dimensional scan is performed to track the pulsatility of blood flow through three-dimensional display. In that case, the three-dimensional scan is carried out with one section scanned a plurality of times, so that three-dimensional pulsatile data is provided with higher precision, thereby leading to a greatly improved diagnostic performance.

The remaining features of the present invention will be clearly understood from the following description of preferred embodiments, which is described together with the accompanying drawings.

BRIEF DESCRIPTION OF THE DRAWINGS

In the accompanying drawings:

FIGS. 4(a) and 4(b) are time-velocity charts depicting the operation of an instantaneous velocity extractor, in which FIG. 4(a) is a chart adopting the latest data from among data groups as an instantaneous velocity and FIG. 4(b) is a chart adopting a central data from among data groups as an instantaneous velocity;

FIGS. 19(a) to 19(c) are illustrations of an electronic scan with the use of a two-dimensional array probe, which is written in comparison with other scan methods;

FIG. 23 is a time-Doppler velocity chart depicting an example in which an image indicative of the pulsatility is unclearly displayed despite that a subject to be examined is pulsated;

FIG. 24 is an illustration in which both of a chart indicating temporal changes in velocities at a pixel pointed by a marker and a pulsatile image are simultaneously displayed;

FIGS. 25(a) to 25(c) are various charts indicating temporal changes in velocities at a pixel pointed by a marker;

FIG. 26 is an illustration outlining how to calculate a velocity, which is adopted in cases where a normalized velocity is used as a corrected velocity;

DETAILED DESCRIPTION OF PREFERRED EMBODIMENTS

With reference to the accompanying drawings, embodiments of an ultrasonic diagnosis apparatus in which the present invention is implemented will now be described in detail.

First Embodiment

An ultrasonic diagnosis apparatus according to a first embodiment of the present invention will now be described with reference to FIGS. 1 to 14.

Figure 1:
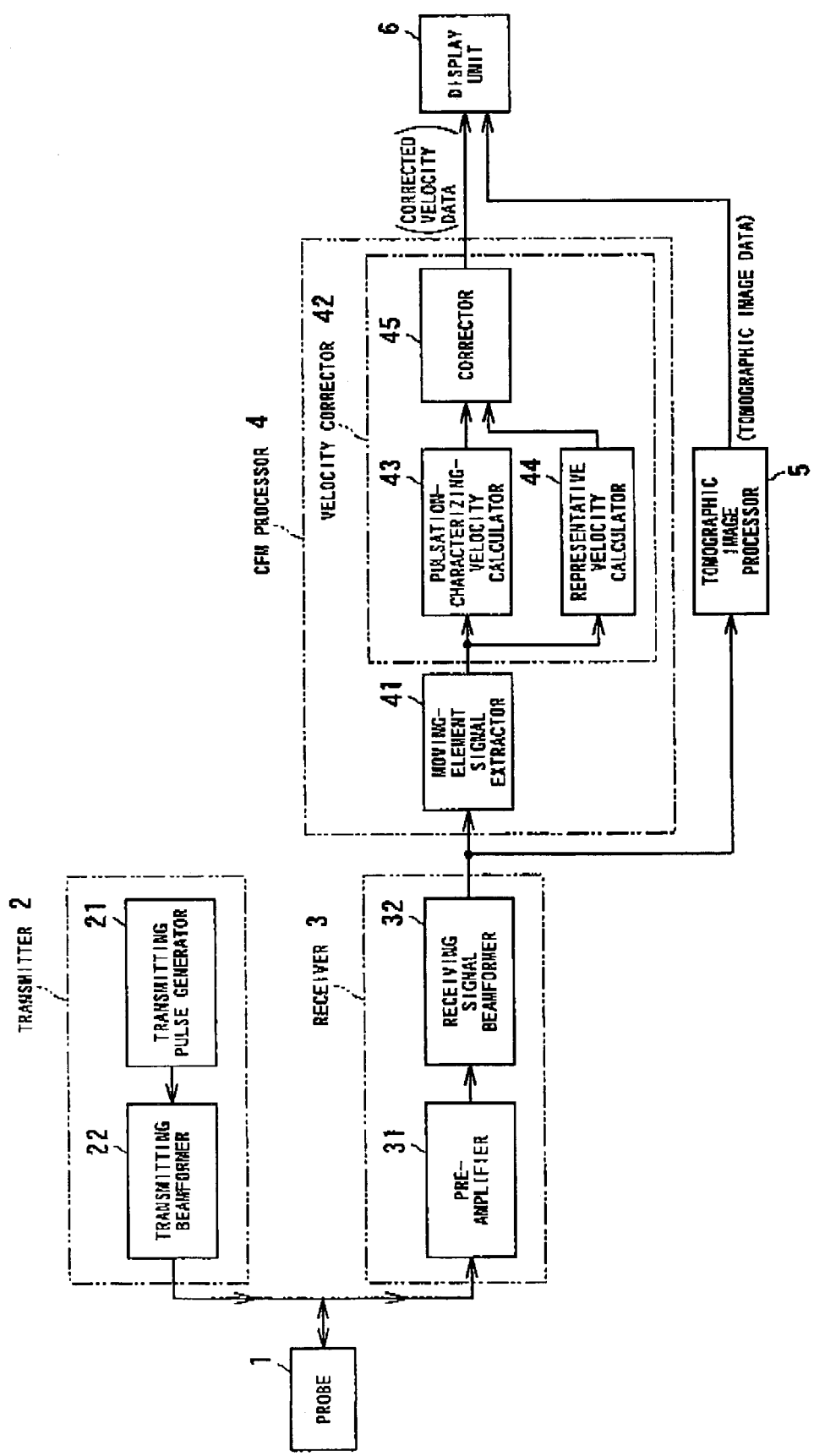
FIG. 1 is a block diagram depicting the entire configuration of an ultrasonic diagnosis apparatus according to a first embodiment of the present invention.

FIG. 1 is a functional block diagram depicting the configuration of the ultrasonic diagnosis apparatus according to this embodiment. As shown in FIG. 1, the ultrasonic diagnosis apparatus according to this embodiment comprises, in addition to an ultrasound probe 1 (hereinafter simply called "probe") made to touch the surface of a subject to be examined, a transmitter 2 and a receiver 3 both electrically connected to the probe 1, a CFM processor 4 and a tomographic image (B-mode) processor 5 both electrically connected to the receiver 3, and a display unit 6 electrically connected to both of the processors 4 and 5.

The probe 1 includes a function of two-way conversion between an ultrasound signal and an electric signal. One example of the probe 1 is configured such that an array type of piezoelectric transducer is linearly set in an array at the distal part of the probe. This array type of piezoelectric transducer is composed of a plurality of piezoelectric elements arrayed in parallel, in which its arrangement direction is assigned to a scan direction. Each of the plurality of piezoelectric elements forms each channel for transmission and reception (i.e., called transmission channel and reception channel).

The transmitter 2, as shown in FIG. 1, comprises a transmitting pulse generator 21 for generating a transmission pulse and a transmitting beamformer 22 for delay-controlling the transmission pulse from the transmitting pulse generator 21 and converting the delay-controlled transmission pulse into a drive pulse applied to each transmission-channel element of the probe 1 for its excitement, Accordingly, the probe 1 is driven, where each piezoelectric element is able to transmit and receive an ultrasound pulse to and from the subject.

The receiver 3, as shown in FIG. 1, comprises a preamplifier 31 placed to each reception channel and a receiving beamformer 32 for performing beam-formation and quadrature phase detection of a signal received by each preamplifier 31. This configuration makes it possible that received resigns are delayed and mutually added to form an echo signal beam-formed in the same direction as that of the transmission. The echo signal is then subjected to generation of an I (In-phase) signal and a Q (Quadrature-phase) signal.

The I and Q signals thus generated make a directional separation of a Doppler signal possible. That is, those signals can be used to determine whether a moving element such as blood flow approaching to the probe 1 or going away from the probe 1. The I and Q signals (hereinafter simply referred as a "Doppler signal") are transmitted to the CFM processor 4 and the tomographic image processor 5, respectively.

The tomographic image processor 5 produces tomographic image data of the subject as a B-mode tomographic image from the received signals obtained through the transmission and reception of ultrasound pulses. The produced tomographic image data are sent to the display unit 6.

The CFM processor 4, as shown in FIG. 1, functionally comprises, from its signal input side, a moving-element signal extractor 41 and a velocity corrector 42. As shown in FIG. 1, the velocity corrector 42 basically comprises calculators 43 and 44 and a corrector 45. One calculator 43 calculates, as a velocity of a moving element within the subject, a velocity indicating characteristics of pulsation (hereafter, the calculator 43 is referred to as "pulsation-characterizing velocity calculator"). The other calculator 44 calculates a representative velocity serving as a reference velocity (hereafter, the calculator 44 is referred to as "representative velocity calculator") 44. The corrector 45 receives calculation results from both of the calculators 43 and 44, where the corrector 45 corrects the calculated velocity indicating characteristics of the pulsation on the basis of the calculated representative velocity.

In this CFM processor 4, the moving-element signal extractor 41 acquires a blood-flow Doppler signal by removing a clatter component signal from the echo signal, and then the blood-flow Doppler signal is sent to the velocity corrector 42. In the velocity corrector 42, the pulsation-characterizing velocity calculators 43 calculates, as a velocity of a moving element based on the present invention, a velocity indicating characteristics of the pulsation, while the representative velocity calculator 44 calculates a representative velocity serving as a reference velocity. In addition, the corrector 45 corrects the velocity indicating characteristics of the pulsation with the use of the representative velocity, so that data of a corrected velocity is produced, and sent to the display unit 6.

The display unit 6 is configured to produce image data in which, for example, image data of CFM blood-flow corrected velocities from the CFM processor 4 are overlaid on tomographic image data from the tomographic image processor 5 and data of a color bar or others showing the amplitude of the corrected velocities are placed thereon. The produced image data is displayed on a monitor. Thus, the corrected velocity data is mapped for display on the monitor, so that the pulsatility can be visualized in an easy and simple way without failure. Blood vessels, such as an artery, portal vein, or vein, can be distinctively displayed, with the result that visibility for various types of blood vessel becomes higher, thus improving a diagnostic performance.

The velocity corrector 42 according to the present invention will now be exemplified in detail.

Figure 2:
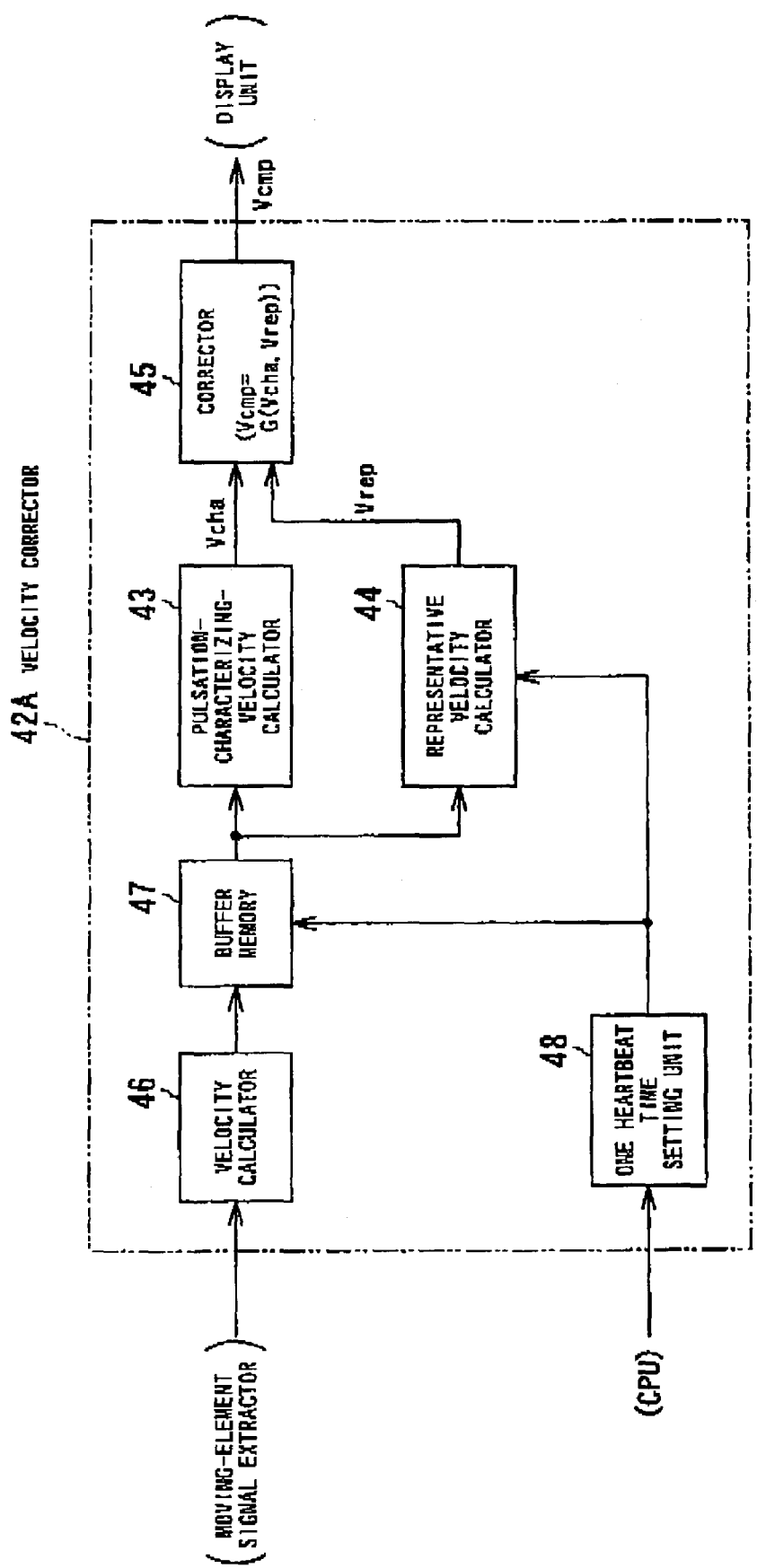
FIG. 2 is a schematic block diagram depicting the velocity corrector.

FIG. 2 is a functional block diagram exemplifying a detailed configuration of the velocity corrector 42 (numbered as a velocity corrector 42A in FIG. 2). The example of the velocity corrector 42A shown in FIG. 2 functionally comprises, in addition to the pulsation-characterizing velocity calculator 43, the representative velocity calculator 44, and the corrector 45, a velocity calculator 46, a buffer memory 47, and a one-heartbeat-period setting unit 48.

In this configuration, a blood-flow Doppler signal at each pixel, which is outputted from the moving-element signal extractor 41 (hereafter this expression will be omitted since the following is concerning the calculation per pixel) is sent to the velocity corrector 42A. In the velocity corrector 42A, velocity data are calculated from the blood-flow Doppler signal at the velocity calculator 46, and the velocity data that has been calculated are temporarily stored in the buffer memory 47.

Velocity data calculated during a period of time of one heartbeat or its equivalent time (hereafter called "one heartbeat time") is stored in the buffer memory 47. Whenever new velocity data comes from the velocity calculator 46, the oldest data in the buffer memory 47 is removed, Hence, in the buffer memory 47, the velocity data is updated in real time, while velocity data acquired during a period of one heartbeat time is held at any time.

Concurrently with the above data update, the pulsation-characterizing velocity calculator 43 operates to obtain a velocity $V_{cha}$ indicating a specified characteristic of the pulsation by extracting it from velocity data acquired during one heartbeat period stored in the buffer memory 47 or from a related group of velocities. The resultant velocity $V_{cha}$ is sent to the corrector 45.

Meanwhile, the representative velocity calculator 44 calculates a representative velocity $V_{rep}$ from velocity data acquired during one heartbeat time in the buffer memory 47, and send the velocity $V_{rep}$ to the corrector 45.

The corrector 45 engages in correcting the velocity $V_{cha}$ indicating the specified characteristic of the pulsation by using the representative velocity $V_{rep}$, providing a corrected velocity $V_{cmp}$. The corrected velocity $V_{cmp}$ is expressed by:

$$V_{cmp} = G(V_{cha}, V_{rep}),$$

where G is a function for the correction. The thus-corrected velocity $V_{cmp}$ is outputted to the display unit 6.

Since the velocity corrector 42 provides the representative velocity $V_{rep}$ every one-heartbeat time, the representative velocity $V_{rep}$ is hardly disturbed by heartbeats. Hence the corrected velocity $V_{cmp}$ in which the nature of the pulsation-characterizing velocity $V_{cha}$ is accurately reflected can be obtained.

In the present embodiment, in response to each time of update on newly inputted velocity data in the buffer memory 47, the velocity $V_{cha}$ indicating a characteristic of the pulsation and the representative velocity $V_{rep}$ are also recalculated for the next update every time new velocity data is received. Consequently, the corrected velocity $V_{cmp}$ is also subjected to recalculation for the next update responsively to the reception of new velocity data. It is therefore possible for the velocity corrector 42 to output the corrected velocity $V_{cmp}$ in real time. The corrected velocity data is thus excellent in the real-time performance.

One heartbeat time in the present embodiment is set to both of the buffer memory 47 and the representative velocity calculator 44 by the one-heartbeat-time setting unit 48. Specifically, the number L of samples obtained during one heartbeat time is set. The number L is obtained by dividing a period of time $T_{HR}$ equivalent to one heartbeat by a sampling time $T_{FR}$ for velocity data. The sampling time shows intervals of time at each of which velocity data is updated, that is, corresponds to a reciprocal number of the number of frames.

Therefore, the calculating equation of the number L of samples is as follows;

$$L = T_{HR}/T_{FR}.$$

Concerning this equation, a period of time $T_{HR}$ corresponding to one heartbeat time is obtained by measuring a period of time of one heartbeat based on an electrocardiographic gating signal obtained from a subject with the use of electrocardiographic gating circuit not shown in FIG. 2. This value of the time $T_{HR}$ is transmitted to the one-heartbeat-time setting unit 48 through a not-shown CPU in FIG. 2. In the case that an electrocardiographic gating signal is not employed, a period of time that is approximately equal to one heartbeat is set to the one-heartbeat-time setting unit 48 with the help of a CPU. A period of time $T_{HR}$ corresponding to one heartbeat is, for example, about one second.

While the present embodiment has been described based on one heartbeat, the present invention is not limited to such a case, but may use a plurality of heartbeats. In the case of a plurality of heartbeats, the time $T_{HR}$ is basically interpreted as being merely repetitions of that obtained in the case of one heartbeat. However, both a velocity indicating the characteristics of the pulsation and a representative velocity are usually unchanged from those values obtained during one heartbeat, thus requiring a larger capacity of the buffer memory 47 if a plurality of heartbeats are employed. Accordingly, it is preferable to use one heartbeat. It is also possible to use an approximate value, which is obtained through averaging based on a shorter period of time less than a period of time of one heartbeat, thus requiring a smaller capacity of the buffer memory 47. In general, it is sufficient if a period of time equal in effect to a mean over a period of time of one heartbeat.

Figure 3:
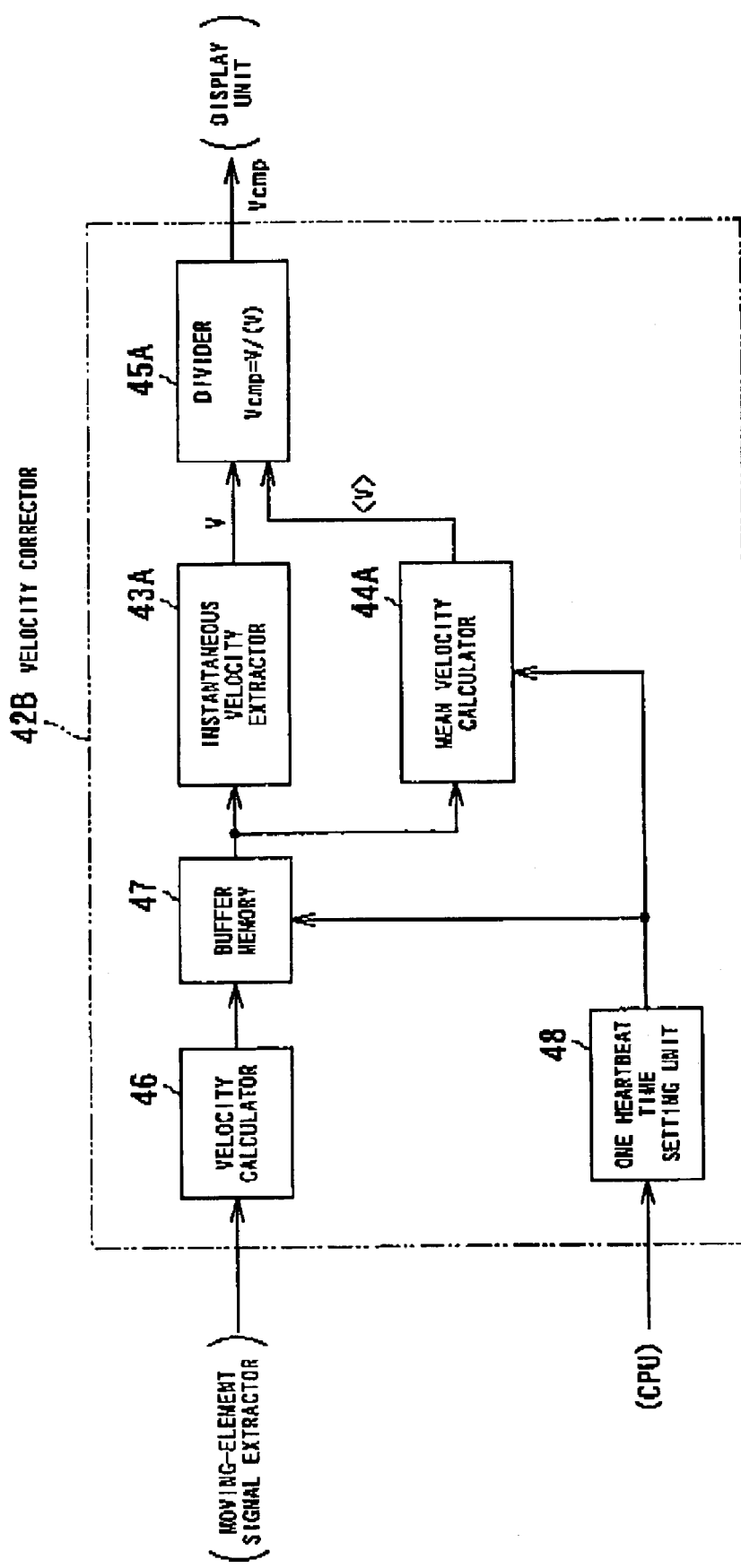
FIG. 3 is a schematic block diagram depicting a practical example of a velocity corrector that divides an instantaneous velocity by a mean velocity.

FIG. 3 is a block diagram depicting a schematic configuration of a velocity corrector 42B, which is another embodiment of the velocity corrector 42A shown in FIG. 2. In FIG. 3, the velocity corrector 42B adopts an instantaneous velocity extractor 43A serving as an embodiment of the foregoing pulsation-characterizing velocity calculator 43, a mean velocity calculator 44A serving as an embodiment of the forgoing representative velocity calculator 44, and a divider 45A serving as an embodiment of the foregoing corrector 45, respectively.

Figures 4A, 4B:
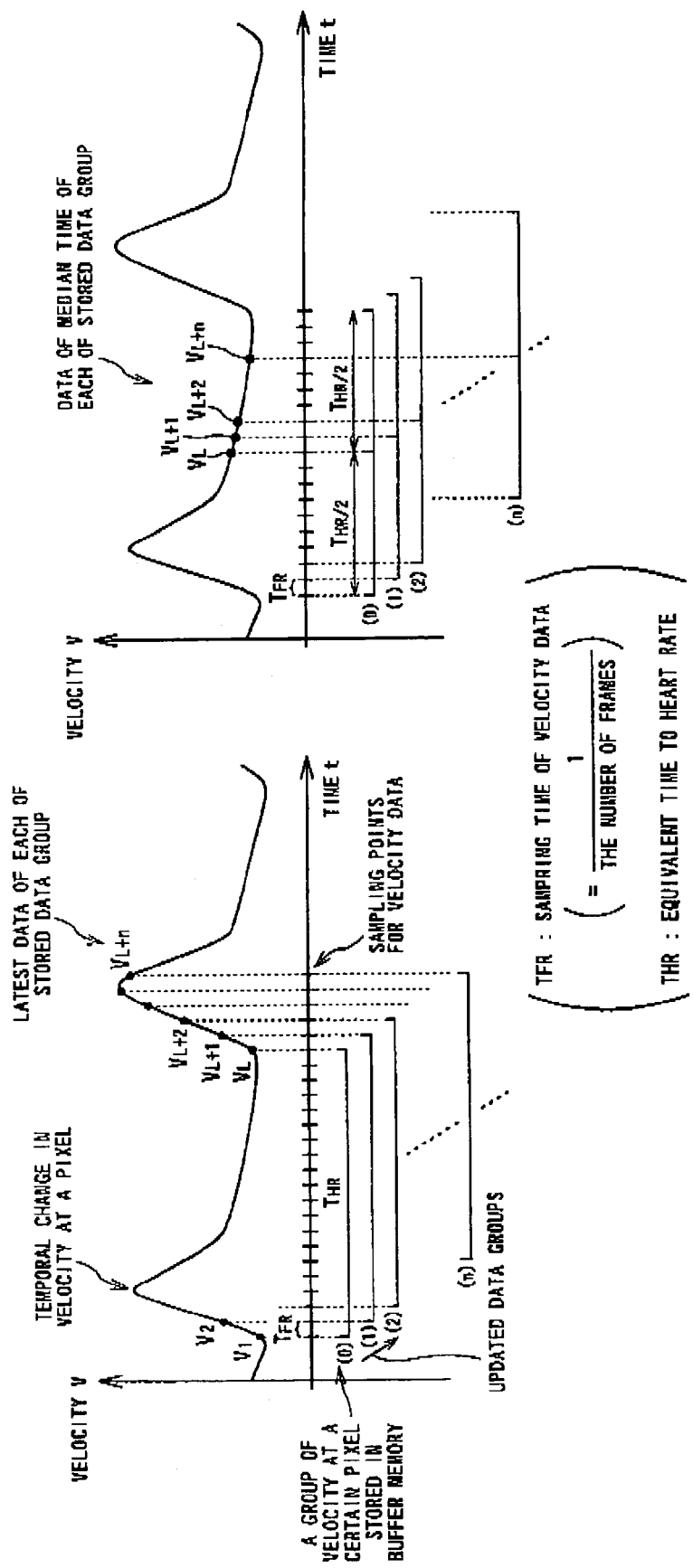

FIGS. 4(a) and 4(b), which illustrate the operation of the instantaneous velocity extractor 43A in the above configuration, are charts depicting a change in velocity V per time t at a certain one pixel constituting an image (hereafter, all charts to FIGS. 4(a) and 4(b) are shown at one pixel).

In FIG. 4(a), $T_{FR}$ indicates a sampling time for velocity data ($T_{FR}$=1/the number of frames), $T_{HR}$ indicates a period of time equivalent to one heartbeat, $V_1, V_2, \ldots, V_L, V_{L+1}, V_{L+2}, \ldots, V_{L+N}$ indicate velocity data sampled per time $T_{FR}$ at a certain pixel, a data group (0) indicates a group of velocities $(V_1, V_2, \ldots, V_L)$ stored in the buffer memory 47 during a period of time equivalent to one heartbeat $T_{HR}$ at a certain time instant, a data group (1) indicates a group of velocities $(V_2, \ldots, V_L, V_{L+1})$ stored later by one frame than a time phase of the data group (0) (data groups (2), ..., (n) in FIG. 4(a) can be explained in the same way).

More specifically, in the data group (1), the oldest data in the data group (0), i.e., $V_1$ is cleared and the latest data, i.e., $V_{L+1}$ is added. The data in the buffer memory 47 are updated in this way in turn.

In FIG. 4(a), the latest data in a data group is adopted as an instantaneous velocity. For example, a velocity $V_L$ in the data group (0) and a velocity $V_{L+N}$ in the data group (n) are adopted as an instantaneous velocity, respectively. Therefore, in the instantaneous velocity extractor 43A shown in FIG. 3, these Velocities $V_L, V_{L+N}, \ldots$ are read out in sequence. In this case, it may be possible to obtain these velocities $V_L, V_{L+N}, \ldots$ directly from the velocity calculator 46 without passing through the buffer memory 47.

Meanwhile, in the mean velocity calculator 44A, a mean value <V> of velocity data over a period of time of one heartbeat is calculated. The mean value <V> can be determined as being any of an mean value of velocities $V_1, V_2, \ldots, V_L$ obtained at each time phase, the absolute value of a mean value of velocities $V_1, V_2, \ldots, V_L$ obtained at each time phase, the mean value of an absolute value of velocities $V_1, V_2, \ldots, V_L$ obtained at each time phase, and an RSM value (Real Mean Square Value) of velocities $V_1, V_2, \ldots, V_L$ obtained at each time phase. Therefore, an equation for calculating a mean value <V> can be determined from the following equations:

$$<V> = (V_1 + V_2 + \ldots + V_L)/L$$

$$<V> = |V_1 + V_2 + \ldots + V_L|/L$$

$$<V> = (|V_1| + |V_2| + \ldots + |V_L|)/L$$

$$<V> = \mathrm{SQRT}\{(V_1^2 + V_2^2 + \ldots + V_L^2)/L\}.$$

In the above equations, L is the number of samples of velocity data over a period of time of one heartbeat at each pixel.

Alternatively, the mean value <V> may be decided as being a value or its absolute value, which is calculated by applying an FIR filter, IIR filter, or nonlinear filter to velocities $V_1, V_2, \ldots, V_L$ obtained at each time phase or their absolute values $|V_1|, |V_2|, \ldots, |V_L|$. If defining a function FIL required for the filtering calculation, equations for the mean value <V> may be exemplified as follows:

$$<V> = \mathrm{FIL}(V_1 + V_2 + \ldots + V_L)$$

$$<V> = |\mathrm{FIL}(V_1 + V_2 + \ldots + V_L)|$$

$$<V> = \mathrm{FIL}(|V_1| + |V_2| + \ldots + |V_L|)$$

$$<V> = |\mathrm{FIL}(|V_1| + |V_2| + \ldots + |V_L|)|.$$

Furthermore, a vectorial mean value or its absolute value of velocities $V_1, V_2, \ldots, V_L$ obtained at each time phase may be set to the mean value <V>. Embodiments of this setting will now be described with the reference of FIGS. 5(a), 5(b) and 5(c).

Figure 5A:
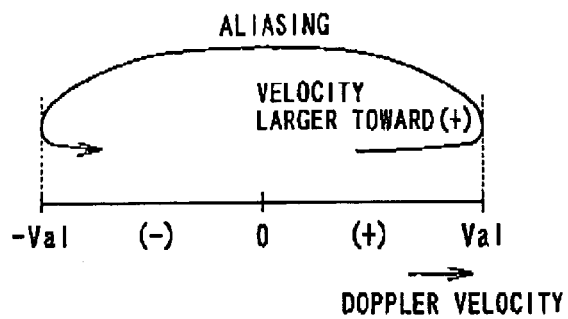
FIGS. 5(a) to 5(c) are views illustrating aliasing with the use of a vectorial mean value or its absolute value as a mean velocity data per a period of time of one heartbeat.
Figure 5B:
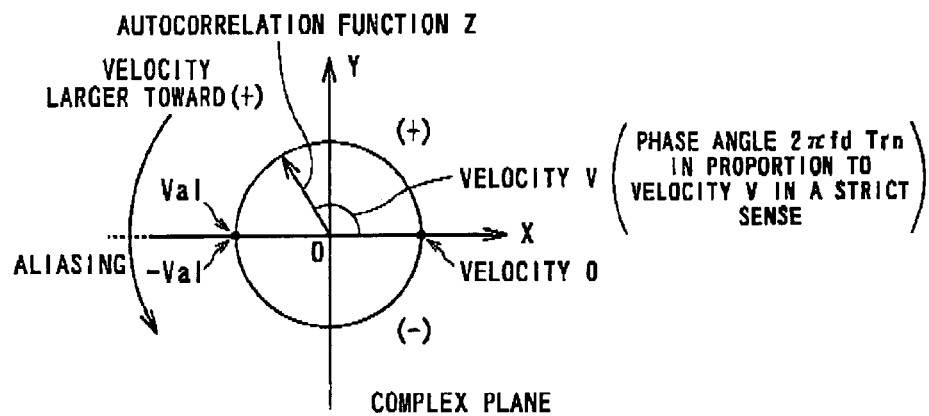
Figure 5C:
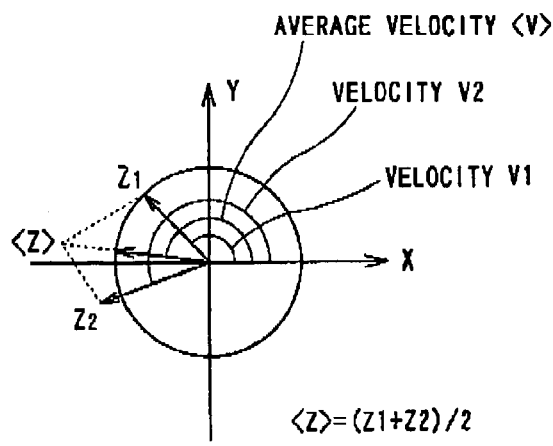

FIGS. 5(a) to 5(c) illustrate aliasing of the Doppler velocity derived by the sampling theorem. In general, an ultrasound pulse is transmitted at predetermined intervals $T_m$, a blood flow Doppler signal to be acquired is formed into a discrete signal consisting of N-pieces of signals that should be mapped at constant intervals $T_m$, if considering one raster. Hence, as shown in FIG. 5(a), the Doppler velocity is folded back at aliasing velocities $V_{a1} = \pm 1/(2T_m) \cdot c/2f_M$. For example, when the velocity increases toward its plus (+) direction, the velocity folds back to the side of $-V_{a1}$ at a position immediately after $+V_{a1}$, and then approaches to zero (0) in the reverse direction along the minus (−) region.

FIG. 5(b) illustrates the same phenomenon with the use of a mean complex autocorrelation function Z on N-pieces of Doppler data defined by the equation (2) described in the section of the background of the invention. The complex autocorrelation function Z may be considered as a vector. In other words, in FIG. 5(b), an increase an a decrease in the velocity means that a vector corresponding to the complex autocorrelation function Z rotates around the origin on the complex plane.

Accordingly, in the case of FIG. 5(b), an angle of rotation of the complex autocorrelation function Z from +X-axis (strictly speaking, a phase angle $2\pi f_d T_m$ that is proportional to the velocity V) corresponds to the velocity V. As a result, the velocity V=0 is located on the +X-axis, while the above aliasing velocity $V = \pm V_{a1}$ are located on the −X-axis. When the velocity V increases in its plus (+) direction so as to pass the −X-axis, the velocity turns from its plus (+) value to its minus (−) value at a boundary of values $V = \pm V_{a1}$.

Therefore, as shown in FIG. 5(c), a mean of velocities $V_1, V_2, \ldots, V_L$ obtained at each time phase can be obtained by adding or averaging complex autocorrelation functions $Z_1, Z_2, \ldots, Z_L$ for each time phase on the same complex plane.

This averaging technique can be understood as a vectorial averaging technique. This averaging is advantageous in that it will not be influenced by aliasing, unless the velocity changes extremely.

Another method of obtaining a mean of autocorrelation functions is that the amplitudes of autocorrelation functions Z are subject to normalization before averaging them. A mean $<Z>$ may be calculated with the use of one of the equations:

$$<Z>=(Z_1+Z_2+\ldots+Z_L)/L$$

$$<Z>=(Z_1/|Z_1|+Z_2/|Z_2|+\ldots+Z_L/|Z_L|)/L.$$

(For example, in the case of FIG. 5(c), a mean $<V>$ of velocities $V_1$ and $V_2$ can be calculated on $<Z>=(Z_1+Z_2)/2$.)

Since the thus-obtained mean $<Z>$ of the autocorrelation functions is expressed as being $<Z>=<X>+j<Y>$, a mean $<V>$ of the velocities V may be calculated by the following equations, if the previously defined equations (2) and (4) in the section of the background of the invention are employed:

$$<V>=c/(2f_M)\cdot(2\pi T_m)^{-1}\tan^{-1}(<Y>/<X>)$$

$$<V>=|c/(2f_M)\cdot(2\pi T_m)^{-1}\tan^{-1}(<Y>/<X>)|.$$

Concerning the embodiment shown in FIG. 3, the above calculation is implemented by storing autocorrelation functions $Z_1, Z_2, \ldots$, which are outputted from the velocity calculator 46, into the buffer memory 47 and by sequentially reading out the autocorrelation functions $Z_1, Z_2, \ldots$ stored in the buffer memory 47 into the mean velocity calculator 44A. This allows the mean velocity calculator 44A to calculate mean values $<V_0>, <V_1>, \ldots$ of velocity data included in each of the data groups (0), (1), ... in turn. Then the divider 45A is allowed to calculate corrected velocity $V_{cmp0}, V_{cmp1}, \ldots$ in turn on the basis of the equations expressed as follows:

$$V_{cmp0}=V_L/<V>_0$$

$$V_{cmp1}=V_{L+1}/<V>_1$$

In these equations, in lieu of the mean values $<V_0>, <V_1>$ of the velocity data which are employed as the denominators, adopting an absolute values of each of the mean values, the corrected velocities $V_{cmp0}, V_{cmp1}, \ldots$ are calculated based on the equations expressed as follows:

$$V_{cmp0}=V_L/|<V>_0|$$

$$V_{cmp1}=V_{L+1}/|<V>_1|$$

The foregoing equations for the corrected velocities provide corrected velocity data with orientation, which has undergone the directional separation by means of the plus or minus sign of an instantaneous velocity appearing as a numerator.

Similarly, in lieu of the corrected velocities $V_{cmp0}, V_{cmp1}, \ldots$, the absolute value of each of the velocities $V_{cmp0}, V_{cmp1}, \ldots$ can be adopted based on the equations expressed as follows:

$$V_{cmp0}=|V_L/<V>_0|$$

$$V_{cmp1}=|V_{L+1}/<V>_1|$$

thus providing the corrected data which indicate their magnitudes only.

In addition, an instantaneous velocity to be sampled is not limited to the latest velocity as described before, but any of data stored in the buffer memory 47 may be usable.

FIG. 4(b) illustrates an example in which a temporally median data of each of the stored data groups (0), (1), ..., (n) is selected as an instantaneous velocity to be sampled. For example, in the case of the data group (0), the temporally central data is data $V_L$ at a median time $T_{HR}/2$ of a period of time $T_{HR}$ equivalent to one heartbeat. In this case, a time lag between a mean velocity obtained by the mean velocity calculator 44A and an instantaneous velocity obtained by the instantaneous velocity extractor 43A is minimized, so that reliability of corrected velocities is advantageously improved.

In the foregoing case of FIG. 4(a), the latest data of each of the stored data groups is selected as an instantaneous velocity to be sampled. Hence a delay time caused by the processes from data acquisition through the probe 1 to its display can be minimized, which provides images with a higher real time performance.

Figure 6:
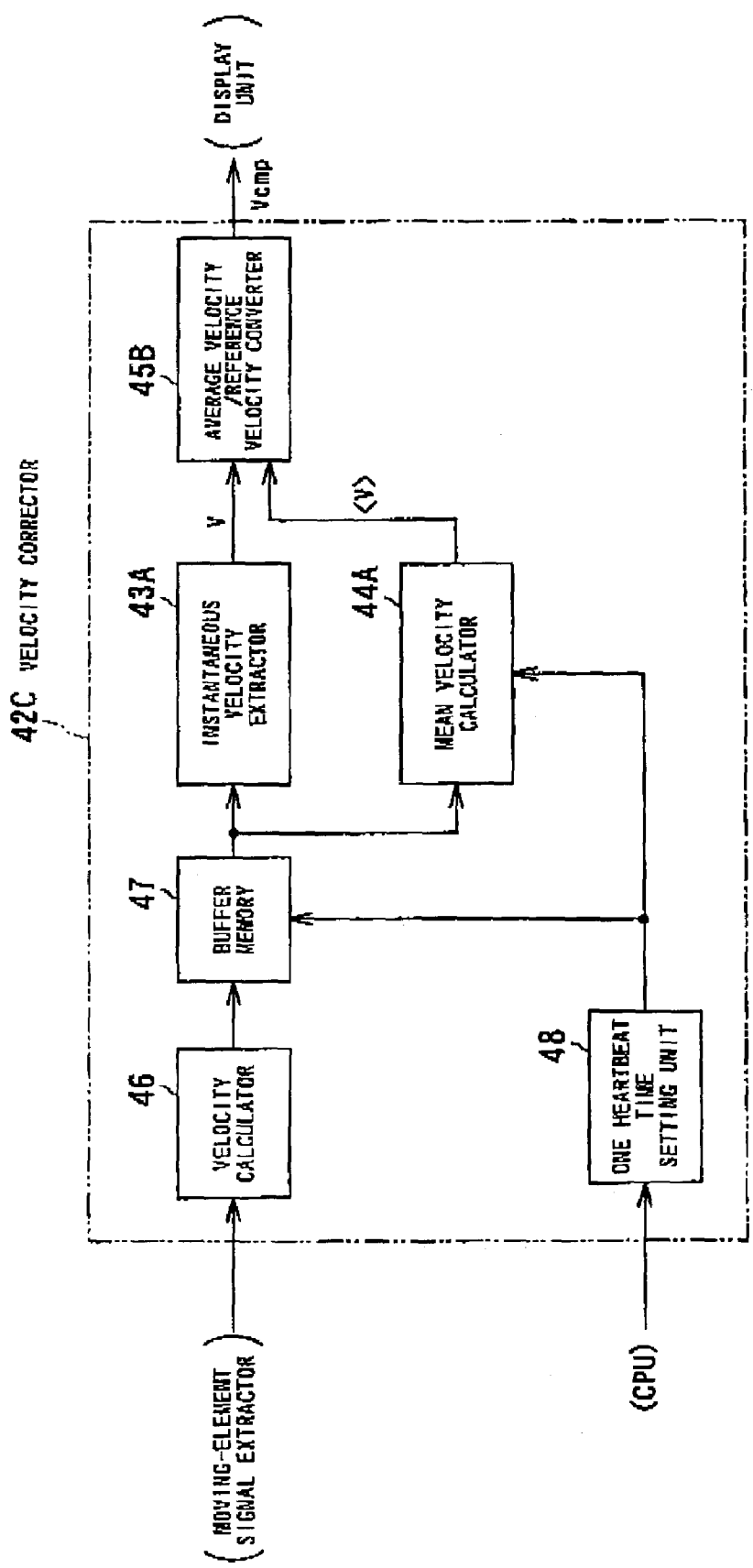
FIG. 6 is a schematic block diagram exemplifying a velocity corrector which converts velocities characteristic of pulsatility to representative reference velocities.

Although the velocity corrector 42B shown in FIG. 3 has used the divider 45A functioning as the corrector 45, the present invention is not limited to this configuration. An alternative configuration can be provided as shown in FIG. 6, where a velocity corrector 42C has a mean velocity/reference velocity converter 45B placed for the divider 45A in FIG. 3. The constituents other than the mean velocity/reference velocity converter 45B in FIG. 6 (that is, the velocity calculator 46, buffer memory 47, one-heartbeat-time setting unit, instantaneous velocity extractor 43A, and mean velocity calculator 44A) are the same in operations as those shown in the foregoing velocity corrector 42B. The correction principle on the mean velocity/reference velocity converter 45B is to divide an instantaneous velocity V by an amount $\zeta$ ($=\zeta\times<V>$) produced by multiplying a mean velocity $<V>$ by a certain constant $\zeta$. This calculation lead to a change in a velocity display range for each pixel.

Specifically, in the case of a calculation technique according to the embodiment in FIG. 6, a value $\zeta<V>$ derived by multiplying a mean velocity $<V>$ by a certain constant $\zeta$ corresponds to a display range ($\zeta$ is a constant independent of the pixels). In addition, a mean velocity $<V>$ which differ from each other pixel by pixel is multiplied by a constant $\zeta$ to produce a velocity range $\zeta<V>$ which differs from pixel to pixel, Then an instantaneous velocity V at each pixel is divided by the velocity range $\zeta<V>$ at each pixel. However, in general, the mean velocity/reference velocity converter 45B operates to covert the instantaneous velocity V into an amount specific to the velocity range $\zeta<V>$ for velocity correction. This correcting example yields a difference in velocity, which is $\zeta$ (a constant) times larger than a velocity corrected by the foregoing dividing technique, but such a difference can be eliminated when being allocated to gradations of a color bar later described.

Since the corrected velocity is originated from a detected velocity, the calculation of a velocity for characterizing characteristics of the pulsation and the calculation of a representative velocity are influenced by aliasing. This aliasing arises theoretically based on the sampling principle. It is therefore impossible to erase its effect completely, but the aliasing can be corrected. One correction technique is the foregoing vectorial calculation, while there are some other correction techniques, which will be described below.

Figure 7:
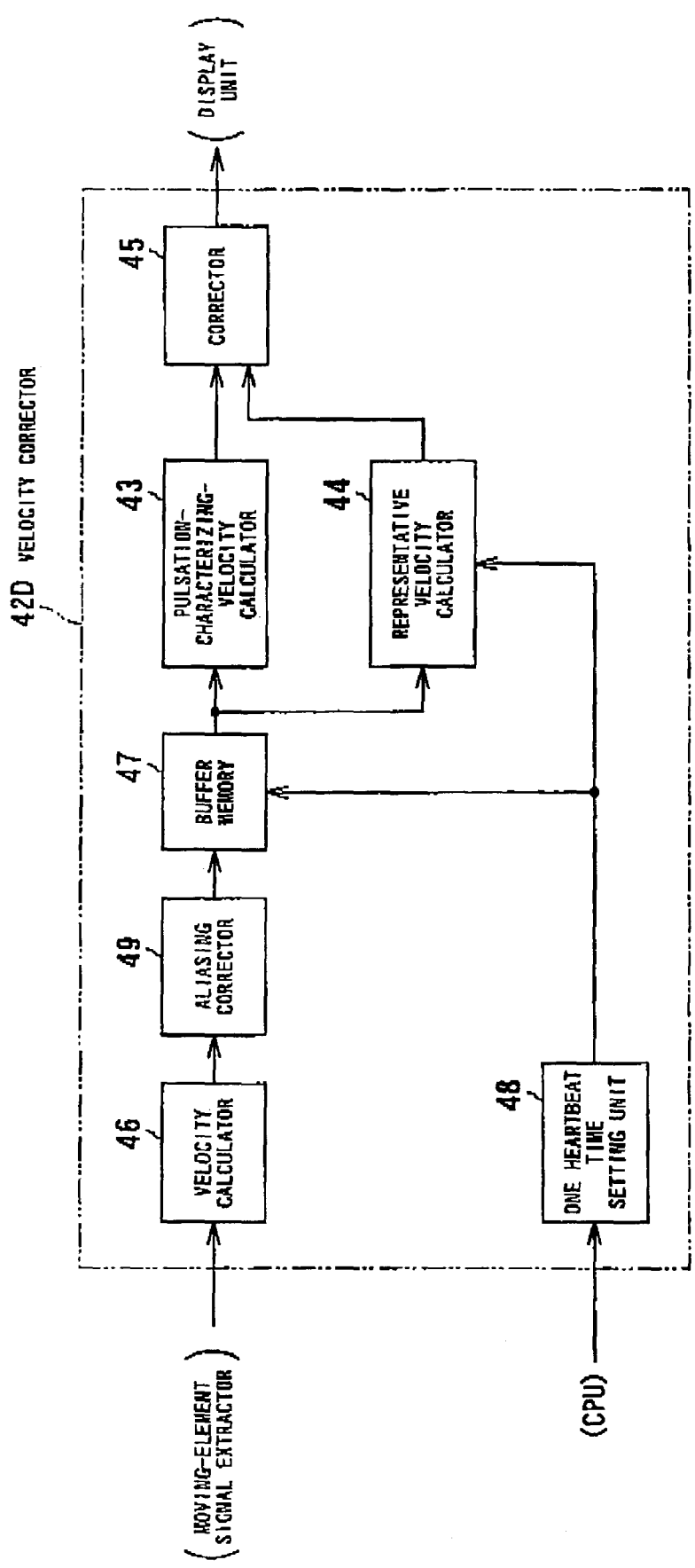
FIG. 7 is a schematic block diagram exemplifying a velocity corrector that has a function of correcting aliasing velocities.

FIG. 7 is a functional block diagram depicting the configuration of a velocity corrector 42D in which an aliasing compensation function is additionally implemented. In the velocity corrector 42D shown in FIG. 7, there is provided the similar configuration of the velocity corrector 42A shown in FIG. 2, in which an aliasing corrector 49 is inserted between the velocity calculator 46 and the buffer memory 47. The other components of the configuration (that is, the pulsation-characterizing velocity calculator 43, representative velocity calculator 44, and corrector 45) are the same in their configurations and operations as those in the embodiment shown in FIG. 2. The aliasing corrector 49 added to this example is responsible for processing for aliasing correction that makes use of physical continuity of a velocity change.

Figure 8:
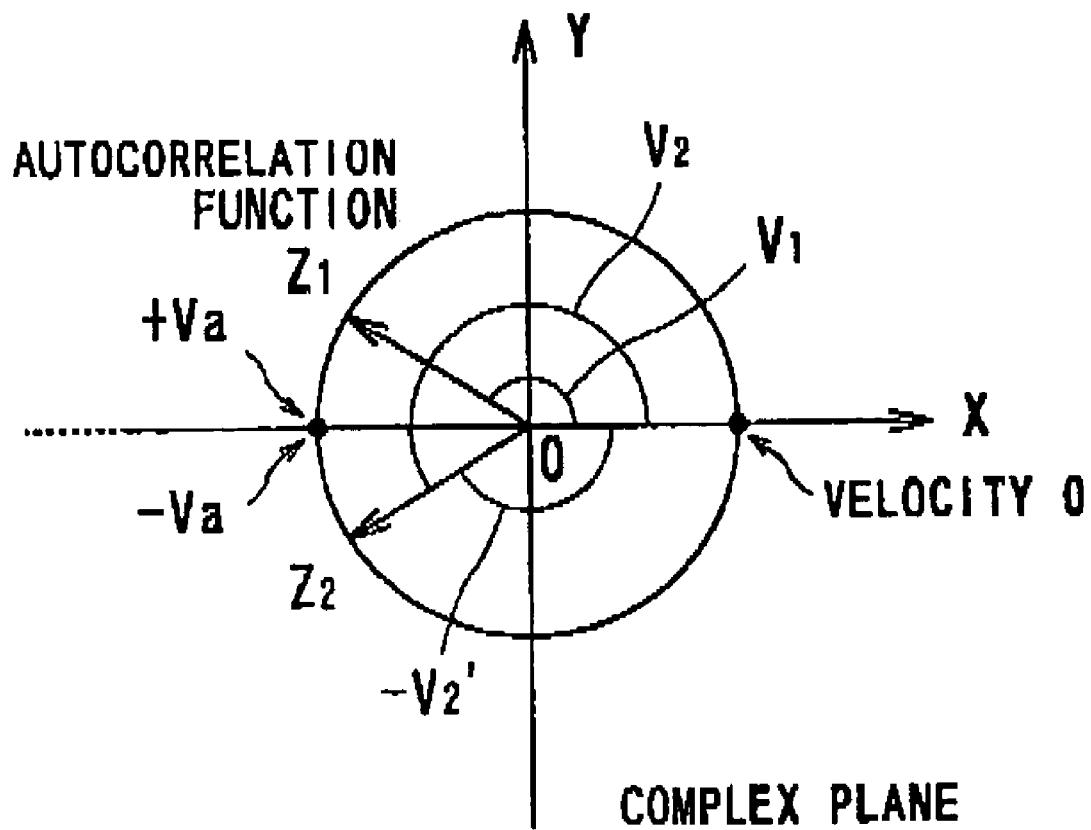
FIG. 8 is a view exemplifying a method of correcting aliasing velocities.
Figures 9A, 9B:
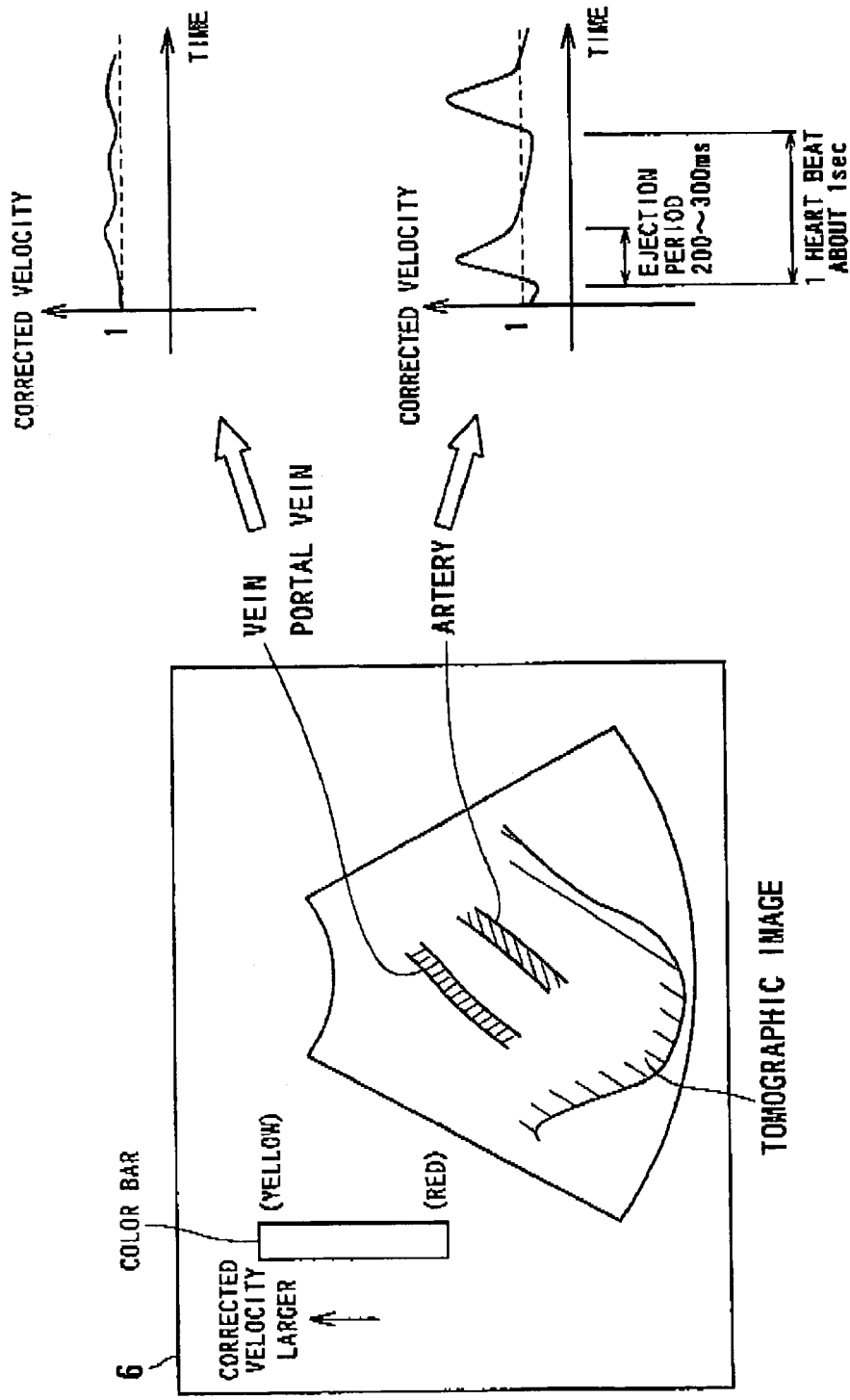
FIG. 9(a) depicts a display example of corrected velocities.
FIG. 9(b) depicts temporal changes in the corrected velocities, corresponding to FIG. 9(a)

FIG. 8 illustrates an example of processing carried out by the aliasing corrector 49, which will be explained with the use of a similar complex autocorrelation function to that shown in FIGS. 5(*b*) and 5(*c*). In this example, an assumption is made in such a manner that, if an interval of time for calculating velocities $V_1, V_2, \ldots, V_L$ at phase times is relatively shorter than changes in the velocity, velocities at mutually adjacent time phases are not so far from each other on the complex plane, whereby aliasing can be corrected. The example shown in FIG. 8 shows a situation where, of two velocities V1 and V2 measured at mutually adjacent time phases, one velocity V1 is free from aliasing, but the other velocity V2 is affected by aliasing to give rise to an erroneous detection of a velocity of $-V_2'$. In such a case, an absolute value of a difference between the velocities $V_1$ and $V_2$ is computed, thus establishing an inequality $|-V_2'-V_1|>Va$. In this case, calculating an equation of $-V_2'+2Va=V_2$ produces $|V_2-V_1|<Va$. When taking the physical continuity of velocity into consideration, it is found that a value of $V_2$ is more probable than a value of $-V_2'$, the value of $V_2$ being adopted.

Based on the above principle, the aliasing is corrected by the aliasing corrector 49. This correction of the aliasing enables a more broadened range of detectable velocities, improving accuracy of velocity to be measured. Accordingly, the detectability for the pulsatility can be enhanced, and a diagnostic performance is also more improved.

The corrected velocity calculated as above is displayed on a screen of the display unit 6. One display example is illustrated in FIG. 9(*a*), in which corrected velocities are overlaid on a tomographic image, but their directions are not separated yet. A color bar in FIG. 9(*a*) shows the amplitudes of the corrected velocities, wherein an exemplified color allocation is such that corrected velocities having smaller amplitudes are depicted in red or similar hue thereto, while corrected velocities having larger amplitudes are depicted in yellow or similar hue thereto.

FIG. 9(*b*) illustrates temporal changes in corrected velocities. This example corresponds to corrected velocities given by the previously described velocity corrector 42B shown in FIG. 3. An amplitude "1" of the corrected velocity in FIG. 9(*b*) shows a mean velocity, as easily understood from the definitional equation (for example, $V_{cmp}=V/<V>$ or others).

As shown in FIG. 9(*b*), in the case of a vein or portal vein, the corrected velocity changes in the neighborhood of the mean velocity "1." In contrast, an artery shows more drastic changes. That is, during one cardiac cycle, the corrected velocity increases sharply over "1" and then decreases sharply in the ejection period, and then gradually decreases along "1" or thereabouts. In other words, the ejection period lasts for 200 to 300 ms, while one cardiac cycle lasts for almost one second. It is therefore understood that a mean velocity over one cardiac cycle is nearer to velocities at time phases belonging to a period during which the velocity gradually decreases.

Hence, it is preferable that a corrected velocity less in amplitude than the mean velocity "1" or thereabouts is displayed in red or reddish hues. In contrast, as a corrected velocity increases gradually larger in amplitude than the mean velocity "1" or thereabouts, the display is made to move from yellowish hues to yellow. Such a display manner is exemplified as shown in FIG. 9(*a*), where a blood vessel, such as an artery, with a stronger pulsatility is depicted in yellowish hues in the ejection period of one cardiac cycle and in reddish hues in the remaining period. In contrast, as shown in FIG. 9(*a*), a blood vessel, such as a portal vein or a vein, which exhibits a less pulsatility is depicted in reddish hues throughout one cardiac cycle. This difference in the depiction of hues makes it possible to distinguishably display the pulsatility, whereby an operator is able to visually distinguish differences in the pulsatility in a clear way.

In this way, the colors assigned to the color bar is decided depending on whether or not a corrected velocity is smaller in amplitude than the mean velocity "1" or thereabouts. When the corrected velocity is higher in amplitude than this threshold, a certain hue and its related hues showing higher velocities are used. When the opposite case to the above comes true, another hue and its related hues showing lower velocities are used. It is thus possible to distinguishably assign the hues to both of the non-pulsatility and pulsatility, thereby providing a visibly easier distinction to pulsated states, thereby contributing to improvement in diagnosis.

FIGS. 10(*a*) to 10(*e*) illustrate examples of color bars that can be displayed.

FIG. 10(*a*) illustrates, like the case shown in FIG. 9(*b*), an example of a color bar that indicates smaller corrected velocities in red, for example, and the hue is shifted to yellow, for example, as the corrected velocity increases. In this embodiment, though the amplitude of corrected velocities is distinguished by differences of hues, the present invention is not limited to this way of display.

FIG. 10(*b*) illustrates another example of display of the color barm, in which the display of power is combined with that of the corrected velocity shown in FIG. 10(*a*). In this example, the larger scattering power of an echo deriving from blood flows, the brighter a hue to be used in the color bar, and vice versa. This manner of displaying the scattering power is able to give the display of vessels a stereoscopic effect, thereby providing a higher visibility to the vessels to be displayed. The power is calculated by a not-shown power calculator installed in the previously described CFM processor 4 in the FIG. 1.

FIG. 10(*c*) exemplifies the display of another color bar, in which directional separation is additionally performed in the display of corrected velocities shown in FIG. 10(*a*). In this case, by way of an example, a flow of blood approaching to the probe 1 is depicted in warm hues, while a flow of blood going away from the probe 1 is depicted in cold hues. This directional separation may make it possible that types of vessels can be distinguished one from the other in an easier manner.

FIG. 10(*d*) also exemplifies another color bar, which is composed by combining the display of directionally separated corrected velocities shown in FIG. 10(*c*) with the display of the scattering power of echo signals. This display configuration is able to have the advantages obtained by both of the examples shown in FIGS. 10(*b*) and 10(*c*).

FIG. 10(*e*) also exemplifies another color bar. In this color bar, a marker indicative of a threshold is added at the boundary between the bones for yellow or yellowish hues and red and reddish hues, which is a display technique adopted by FIGS. 10(*a*) to 10(*d*) for displaying the corrected velocities.

By the way, the present embodiment has adopted the correction of aliasing of velocities, but it is still impossible to correct the aliasing perfectly. It is therefore better for an operator to cope with such an imperfect corrected state of the aliasing on the monitor of the display unit 6. To realize this assist, aliasing velocities providing a region of velocities defined by the sampling principle are depicted on the monitor.

For example, as previously described FIGS. 5(a) to 5(c), the aliasing velocities are $+V_{a1}$ and $-V_{a1}$, so those values are displayed on the monitor. Alternatively, the velocity range may be broadened by an amount of $\Delta V$ in either of (+) or (−) direction. For example, in cases where the range is broadened in the (+) direction, the range is changed from a new range of "$-V_{a1}+\Delta V$" to "$+V_{a1}+\Delta V$." Those new values are preferably depicted on the monitor.

Since it is usual that an operator knows an approximate detectable velocity range, the operator may additionally adjust the aliasing velocity by operating a not-shown button on an operation panel. The aliasing can therefore be avoided with higher precision. Hence, images that are more suitable to higher accurate diagnosis can be obtained.

Further, since the pulsatility is originated from the pumping action of the heart, its characteristic aspect is typically seen during an ejection period of one cardiac cycle. That is, as described before, while the velocity of blood flow through veins and portal veins is almost even throughout one cardiac cycle, the velocity of blood flow through arteries rapidly increases in the ejection period, and then gradually decreases until the next ejection period. For detecting the pulsatility, therefore, it is essential to track the ejection period with certainty. For this purpose, it is preferable that a cross section of a subject is scanned at the number of frames higher than a reciprocal number of a period of time equal to the ejection period of the heartbeat. This way of scanning enables the ejection period to be tracked without failure, thus the pulsatility being depicted more certainly.

The effect obtained from the display of corrected velocities according to the present embodiment will now be described in comparison with that of the conventional one.

Figure 11B:
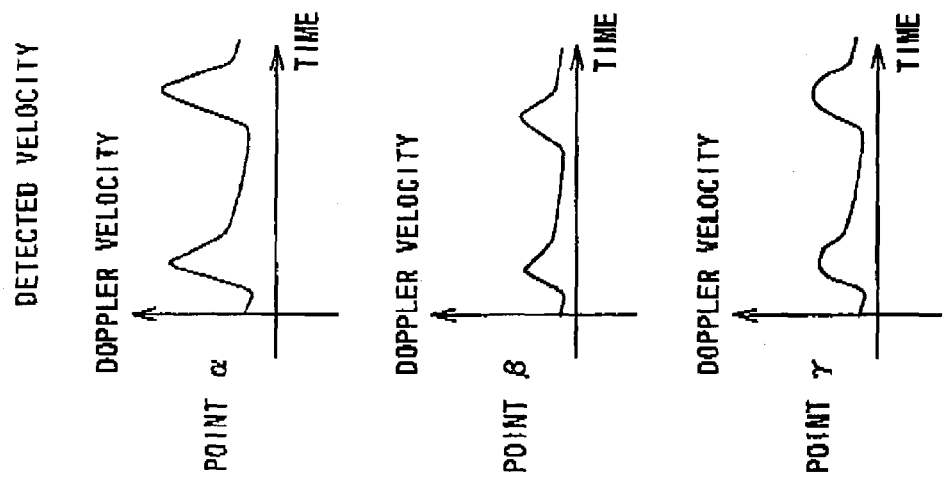
FIGS. 11(a) and 11(b) illustrate an artery displayed on a conventional velocity mode.
Figure 11A:
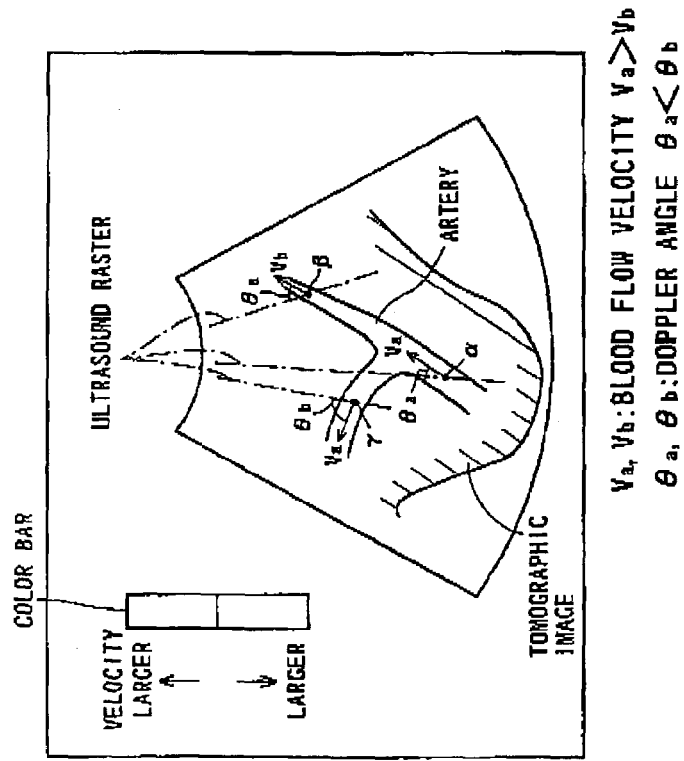

FIGS. 11(a) and 11(b) illustrate the display of an artery depicted on the conventional velocity mode. FIG. 11(a) illustrates an embodiment of such display on a monitor. In FIG. 11(a), each arrow indicates a blood flow velocity (direction and magnitude) of each of positions α, β and γ located differently on the artery depicted on the monitor. The magnitudes of the velocities are $V_a$, $V_b$, and $V_a$, respectively, and the angles (Doppler angles) formed between ultrasound rasters and blood flows are $\theta_a$, $\theta_a$, and $\theta_b$, respectively. In this embodiment, it is assumed that the relationships of $V_a > V_b$ and $\theta_a < \theta_b$ are realized.

FIG. 11(b) shows each blood flow Doppler velocity at each of the positions α, β and γ, i.e., each of temporal changes in raster-directional signal components "$V_a \cdot \cos(\theta_a)$," "$V_b \cdot \cos(\theta_b)$," and "$V_c \cdot \cos(\theta_c)$" of blood flow velocities at the positions α, β and γ. Since each chart in FIG. 11(b) is concerning the same blood vessel (artery) shown in FIG. 11(a), temporal changes in a Doppler velocity at each position should be nearly the same, if they are measured actually. However, because the velocity magnitudes are obtained through proportional calculation, it is found that the magnitudes differ from each other position by position. Accordingly, the conventional velocity display will give rise to the situation where the pulsatility on the same artery is depicted differently from each other position by position, as described before, despite that the pulsatility is originally the same on the same artery.

Practically, as shown in FIGS. 11(a) and 11(b), at such positions as a narrow vessel of which blood velocity is slower (for example, at the position β) or a vessel of which Doppler angle is larger (for example, at the position γ), the resultant pulsatility is depicted smaller than it is originally. Therefore, it is actually difficult that the pulsatility at those points is distinguished visually from blood vessels that exhibit a weaker pulsatility. In addition, a color bar is displayed which depicts velocities, for example, in gradually changing hues from "velocity zero" to positive and negative aliasing velocities. This results in that the position α is visualized using a hue showing a faster velocity and the positions β and γ are visualized using other hues showing a slower velocity, making the discrimination of blood vessels more difficult. On top of it, the range displayed by the color bar and/or how to display on the color bar are not always suitable for the display of the pulsatility and the display itself on the color bar is difficult to understand when viewed. Under such circumstances, it was not easier to correctly interpret the pulsatility on the conventional velocity mode.

Figure 12B:
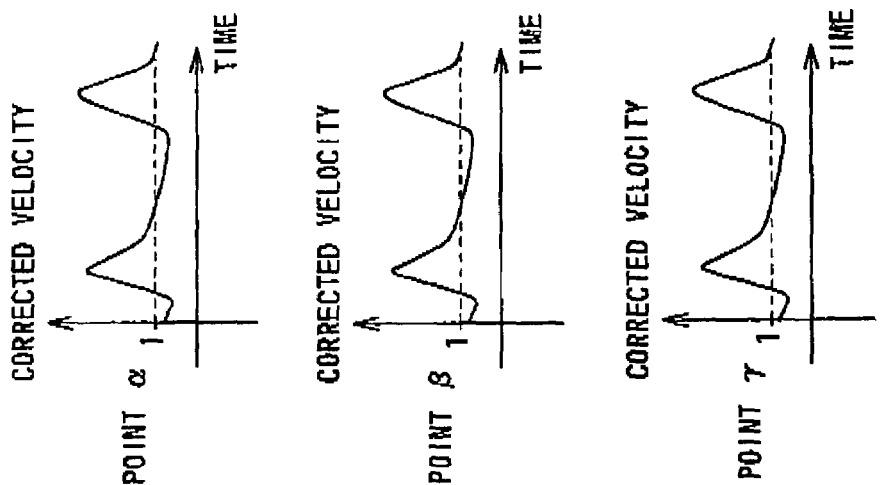
FIGS. 12(a) and 12(b) are views illustrating the display of the same artery as shown in FIG. 11, which are displayed using corrected velocities obtained according to the present invention.
Figure 12A:
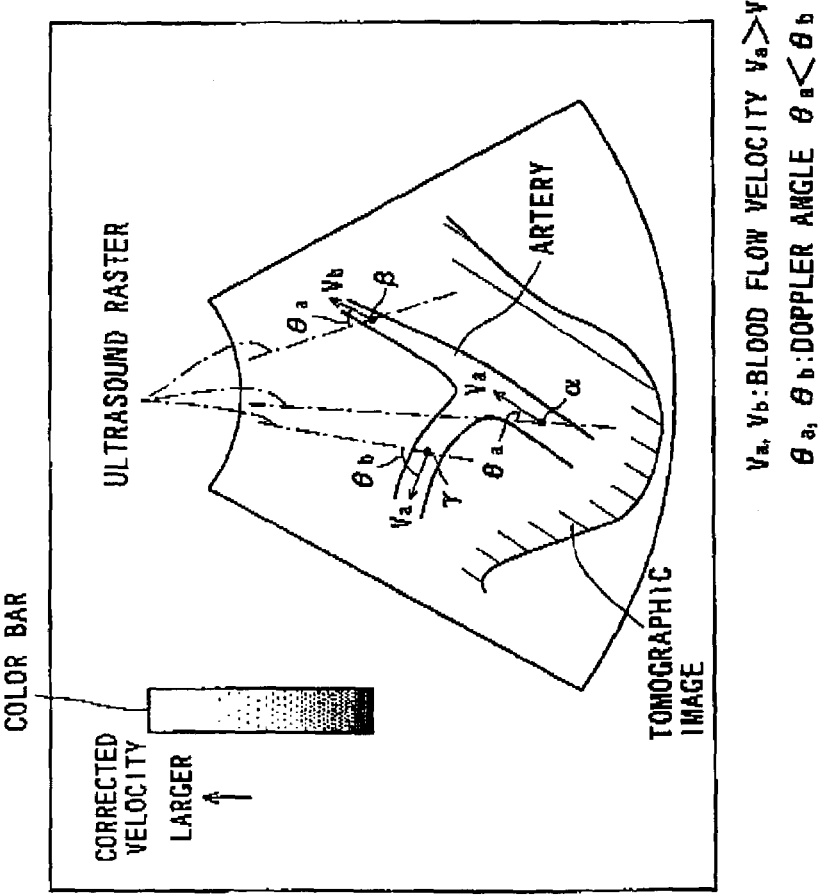
Figure 13:
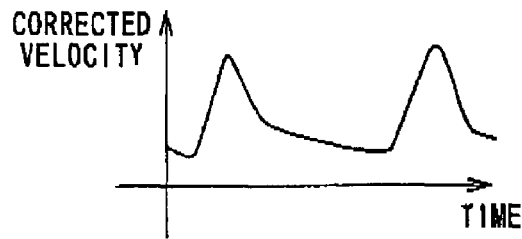
FIG. 13(a) is a chart depicting non-moderated temporal changes in corrected velocities.
FIG. 13(b) is a chart depicting moderated temporal changes in corrected velocities.
FIG. 13(c) is a block diagram depicting a schematic configuration of a principal part of a display unit which has a function of moderating changes in corrected velocities.
Figure 13:
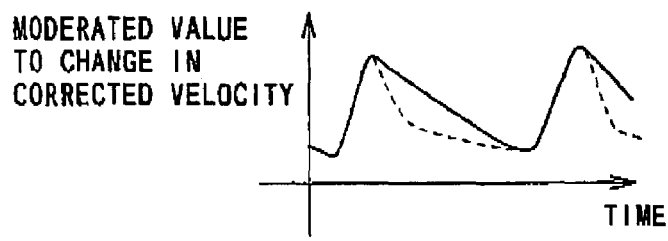
Figure 13:
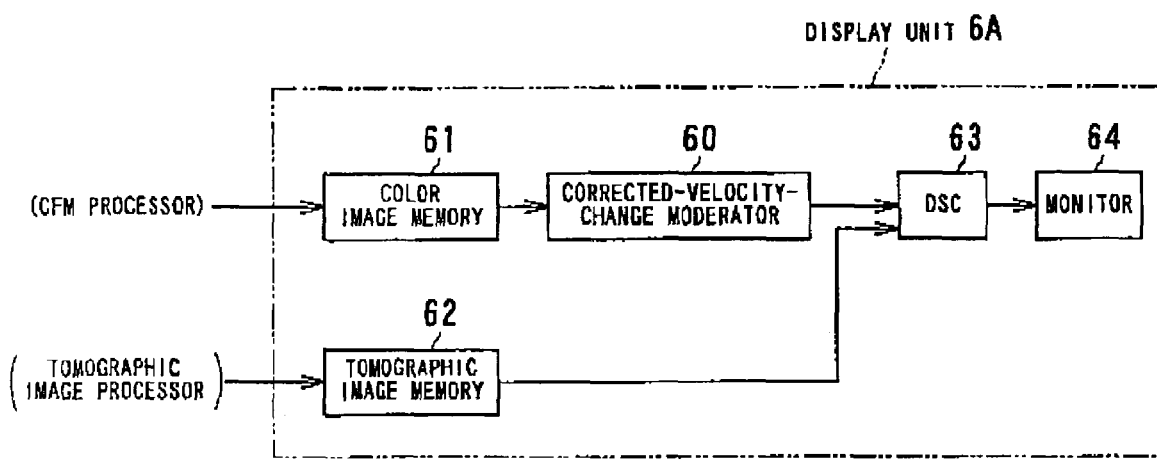

On the other hand, FIGS. 12(a) and 12(b) illustrate the display of corrected velocities according to the present invention, which track and depict the same artery as that shown on the conventional (shown in FIGS. 11(a) and 11(b)). FIG. 12(a) exemplifies an image displayed on a monitor, in which there is a color bar with no directional separation, which is shown similarly to the foregoing embodiments shown in FIGS. 9(a) and 10(a). FIG. 12(b) illustrates temporal changes in blood-flow Doppler velocities "$V_a \cdot \cos(\theta_a)$," "$V_b \cdot \cos(\theta_b)$," and "$V_c \cdot \cos(\theta_c)$" at the respective points α, β, and γ, which have been corrected by means of the previously described velocity correction technique.

As shown in FIGS. 12(a) and 12(b), all the corrected velocities are nearly the same, as long as the same vessel is concerned. In other words, all of a thinner and smaller-Doppler-angle portion (like the position α), a thinner portion (like the position β), and a larger-Doppler-angle portion (like the position γ) provides the same behavior in corrected velocities. That is, the corrected velocities can be nearly "1" in their gradually-decreasing ranges and nearly the same value larger than "1" in their strongly pulsated ranges.

It can therefore be concluded that the velocity mode of the present embodiment is independent on flow velocities and Doppler angles, thus providing approximately equal corrected velocities, thus depicting almost the same pulsatility, as long as the same vessel is subjected to display. When such corrected velocities are subjected to the display with the use of the foregoing color bars, the display is independent on velocities and Doppler angles, thus the pulsatility being depicted clearly with largely improved visibility. In particular, under the velocity display mode according to the present embodiment, the pulsatility can be detected even for blood flows, such as blood flows whose velocities are slower, which are therefore sometimes difficult to be distinguished from non-pulsated vessels, or another blood flow subjected to larger Doppler angles. This is able to give images an effective depiction, thus contributing to greatly improved diagnosis.

Besides, as described above, a larger change in the pulsatility appears during the ejection period lasting 200 to 300 ms at most. Hence, it may feel short for a viewer when visually observing the pulsatility as it is displayed. In such a case, as exemplified in FIGS. 13(a) through 13(c), moderating changes in corrected velocities is effective for making visual observation easier.

FIGS. 13(a) and 13(b) exemplify temporal changes in corrected velocities with no velocity moderation and with velocity moderation, respectively. In this example, to steadily understand the pulsatility from the corrected velocities shown in FIG. 13(a), moderation processing is performed in a way shown in FIG. 13(b). Specifically, through the moderation processing, the temporal changes in the corrected velocity are left without any processing during its rising range, but such changes are moderated so as to moderately decrease during its descending region, with a sharp fall being suppressed. This moderation technique allows visibility for the pulsatility to be enhanced, because there is provided a feeling of afterimage on images to be displayed.

Such moderation processing can be performed by, for instance, the foregoing display unit 6. For realizing the moderation, the display unit 6 is configured as exemplified in FIG. 13(c). The display unit 6 has, as shown in FIG. 13(c), not merely a known configuration including a color image memory 61, tomographic image memory 62, DSC (Digital Scan Converter) 63, and monitor 64 but also a corrected-velocity-change moderator 60 inserted between the color image memory 61 and the DSC 63.

In this configuration, the corrected velocity data transmitted from the foregoing CFM processor 4 is temporarily stored in the color image memory 61. A plurality of frames of data is thus stored in the color image memory 61. The corrected-velocity-change moderator 60 reads out data from the color image memory 61 to conduct the above-mentioned moderation processing, and output resultant data to the DSC 63. Apart from this, the tomographic image data transmitted from the foregoing tomographic image processor 5 is stored in the tomographic image memory 62, before being outputted to the DSC 63.

In the DSC 63, in addition to predetermined image processing, raster conversion and other types of processing, a corrected-velocity image that have experienced the moderation processing in the corrected-velocity-change moderator 60 is overlaid on a topographic image from the tomographic image memory 62. The resultant image data is then sent to the monitor 64 so that an synthesized image is depicted thereon.

In addition, the present embodiment has adopted the CFM processor 4 that has the function of correcting velocities of blood-flow Doppler signals. An alternative is that such function is given to for example the display unit 6, of which configuration is shown in FIG. 14.

Figure 14:
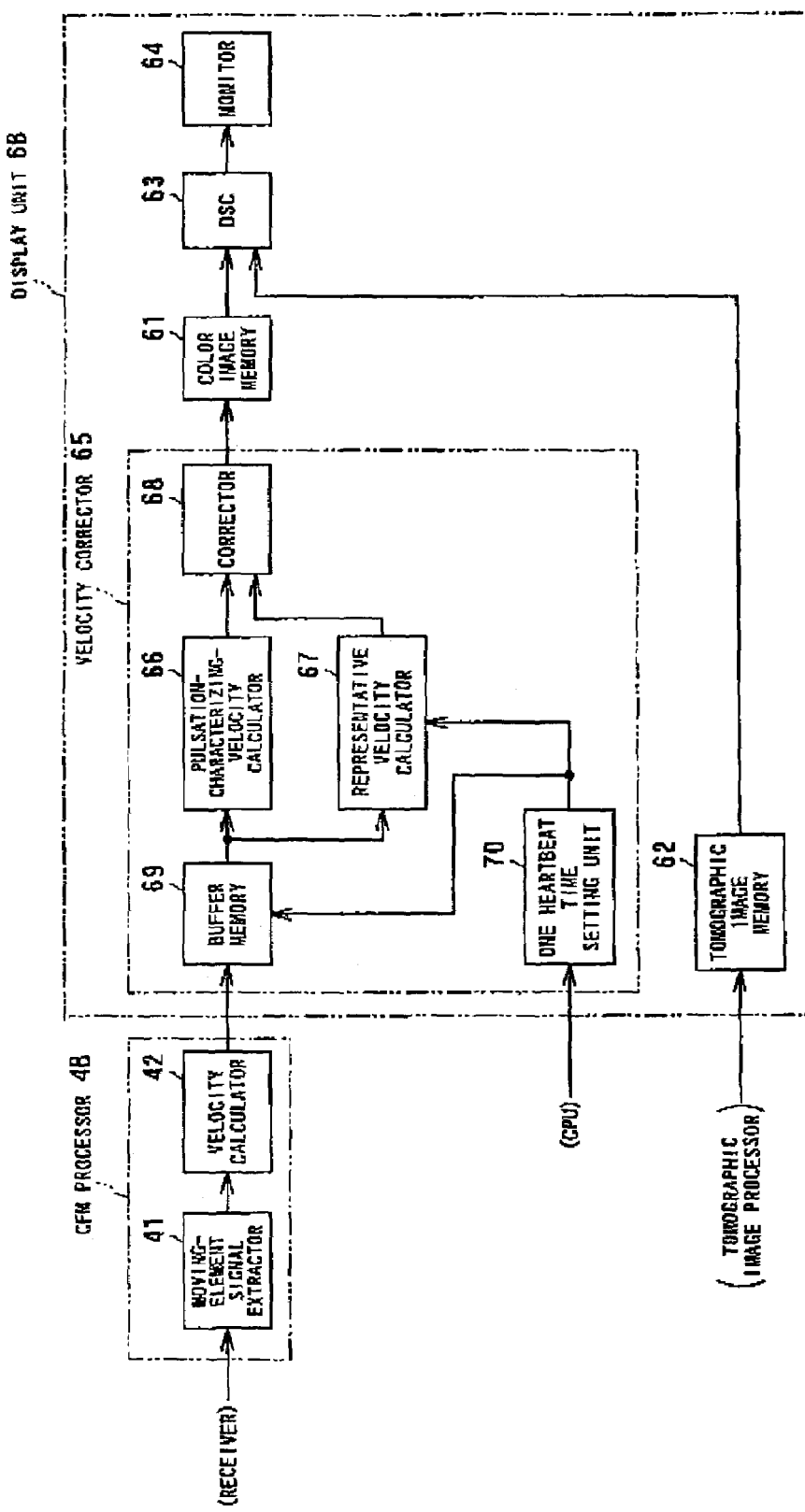
FIG. 14 is a schematic block diagram depicting exemplifying a display unit that has a velocity corrector.

The configuration shown in FIG. 14 comprises a CFM processor 4B configured in a similar way to the conventional to have the moving-element signal extractor 41 and the velocity corrector 42 that outputs corrected velocity data. Furthermore, a display unit 6B is also included in the configuration in FIG. 14, and the display unit 6B is additionally equipped with a velocity corrector 65, in addition to the foregoing known confirmation including the color image memory 61, tomographic image memory 62, DSC 63, and monitor 64. The velocity corrector 65, which is located just before the color image memory 61, is configured similarly to the foregoing velocity corrector 42A placed in the foregoing CFM processor 4. The velocity corrector 65 includes a pulsation-characterizing velocity calculator 66, representative velocity calculator 67, corrector 68, buffer memory 69, and one-heartbeat-time setting unit 70. This configuration also enables the display of pulsatility in a similar way to that described before and provides the advantages identical to those described before.

Second Embodiment

Referring to FIGS. 15 to 22, a second embodiment of the ultrasonic diagnosis apparatus according to the present invention will now be described. The present embodiment concerns a configuration in which the correction of the foregoing blood-flow Doppler signals is applied to three-dimensional display.

Figure 15:
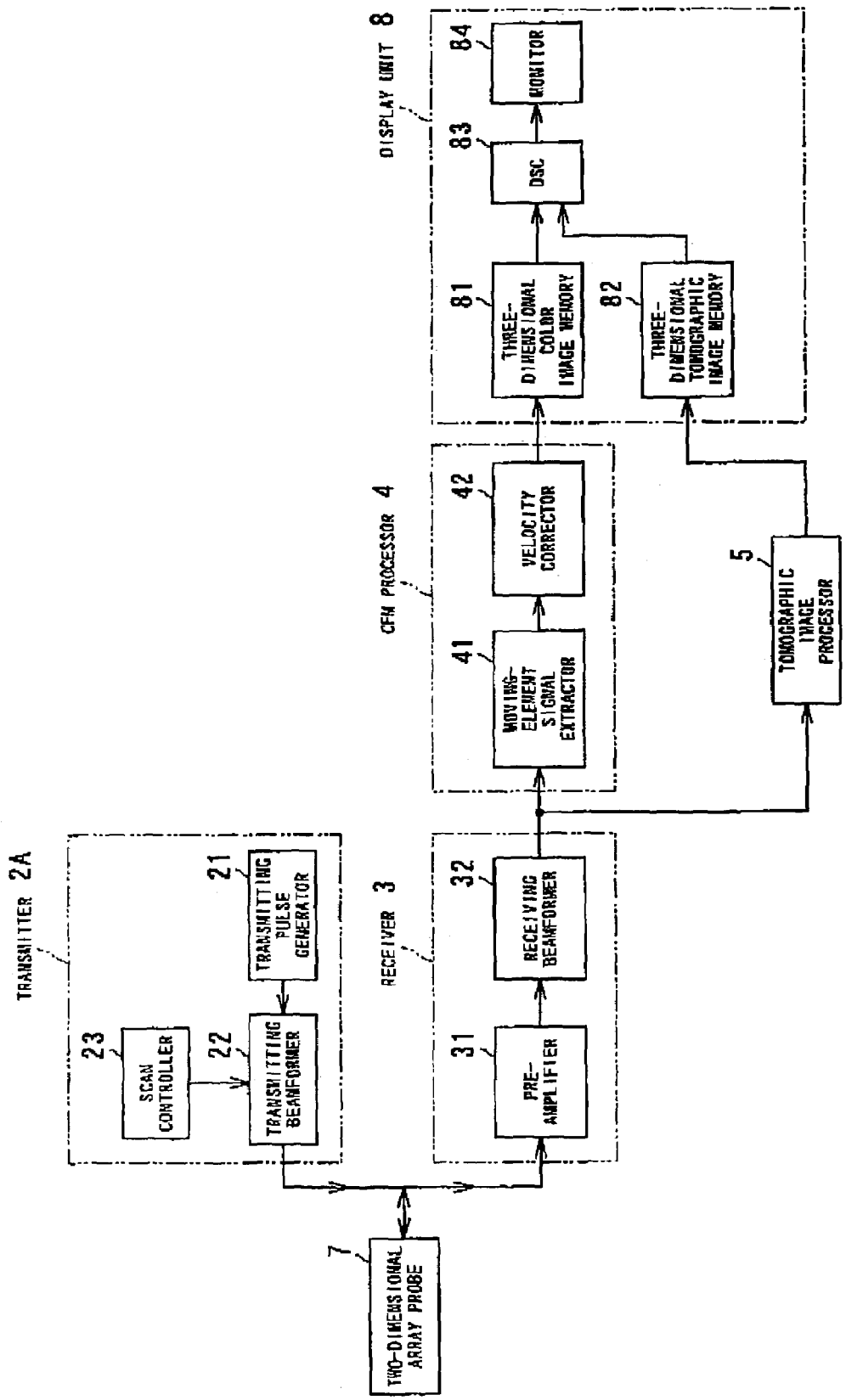
FIG. 15 is a schematic block diagram depicting an entire configuration of an ultrasonic diagnosis apparatus according to a second embodiment of the present invention.

FIG. 15 shows the functional block diagram of the ultrasonic diagnosis apparatus that will be described below. As shown in FIG. 15, the ultrasonic diagnosis apparatus adopts a two dimensional array probe 7 as a probe made to touch to the surface of a subject to be examined.

As the remaining constituents, the ultrasonic diagnosis apparatus includes, as shown in FIG. 15, of a transmitter 2A and a receiver 3A, both of which are electrically connected to the two-dimensional array probe 7. The apparatus further includes a CFM processor and a topographic image processor 5, both of which are electrically connected to the receiver 3A, and a display unit 8 electrically connected with both the processors 4 and 5. Of these constituents, the transmitter 2A includes, in addition to the transmitting pulse generator 21 and the transmitting beamforner 22, which are identical to those in FIG. 1, a scan controller 2C to be added. The receiver 3A includes the preamplifiers 31 and the receiving beamformer 32, like the configuration in FIG. 1. The CFM processor 4 includes, like the configuration in FIG. 1, the moving-element signal extractor 41 and the velocity corrector 42. Furthermore, the display unit 8 includes, in addition to the DSC 83 and monitor 84 that have been described in FIG. 13(c), a three-dimensional color image memory 81 and a three-dimensional tomographic image memory 82. (The constituents similar or identical to those described before will be omitted from being explained below or will be explained just briefly.)

The two-dimensional array probe 7 has a function of two-way conversion between ultrasound signals and electric signal. To be specific, the probe 7 has a two-dimensional array type of piezoelectric transducer two-dimensionally placed at the tip. The a two-dimensional array type of piezoelectric transducer is formed by mapping a plurality of piezoelectric elements two-dimensionally, that is, like a matrix, so that a ultrasound beam signal can be scanned three-dimensionally, including the longitudinal, lateral, and oblique directions. A plurality of piezoelectric elements constitute transmitting and reception channels, respectively.

Hence, the two-dimensional array probe 7 is allowed to scan a plurality of sections located within a subject, as sections to be scanned are changed (i.e., a "volume scan" is performed), with the result that three-dimensional data (i.e., volume data) can be acquired. The volume scan is exemplified as various forms, as shown in FIGS. 16(a) to 16(c) and FIGS. 17(a) to 17(c).

Figure 16A:
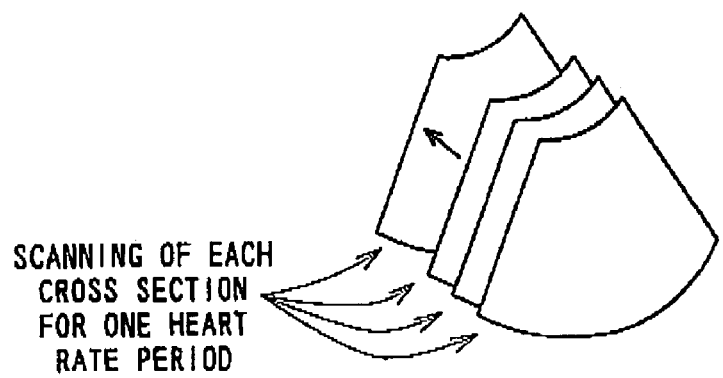
FIGS. 16(a) to 16(c) illustrate some examples of a volume scan.

FIG. 16(a) explains a scan technique by which a section to be scanned is shifted along a perpendicular direction to the section during its scanning operation. Meanwhile, FIG. 17(a) explains another scan technique used in such a manner that a section to be scanned is shifted to rotate about its central axis during its scanning operation. When either technique is used, it is required that a single section be scanned a plurality of times, preferably, a plurality of times during a period of one heartbeat. This scanning is one of the characteristic inherent to present invention.

Figure 16B:
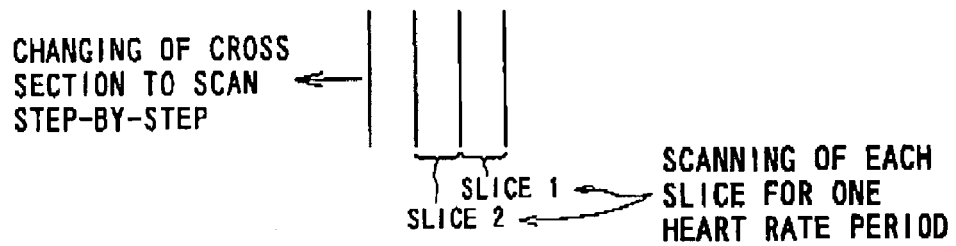
Figure 16C:
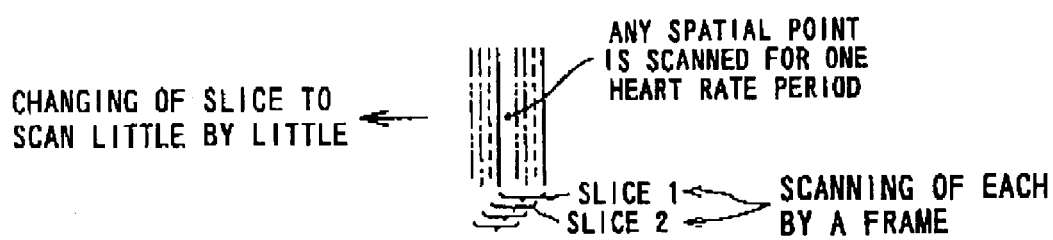
Figure 17A:
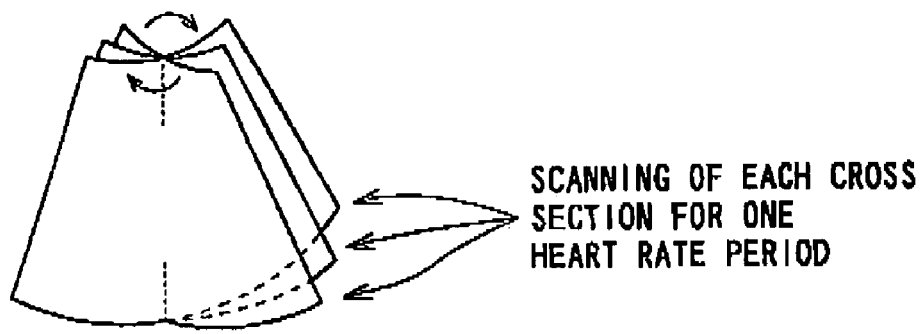
FIGS. 17(a) to 17(c) illustrate other examples of the volume scan.
Figure 17B:
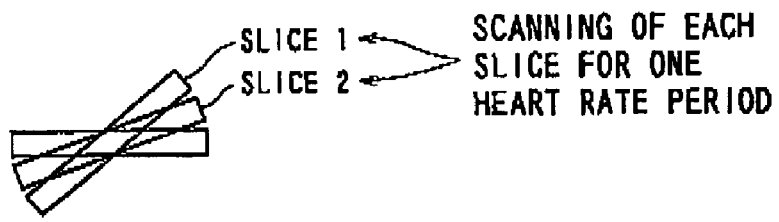
Figure 17C:
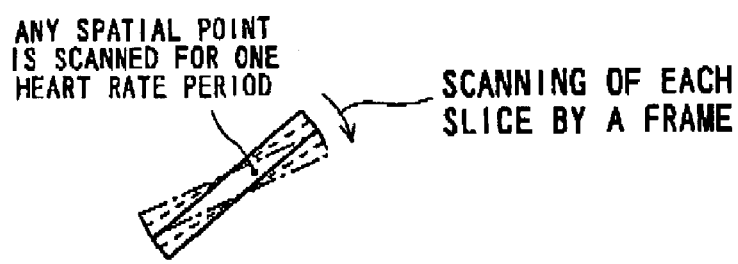

One scanning example is shown in FIGS. 16(b) and 17(b), respectively, wherein an ultrasound beam scans a certain section during a period of one heartbeat, and then the ultrasound beam is shifted by a width equal to a beam thickness to scan the next section in the same manner. Another scanning example is shown in FIGS. 16(c) and 17(c), respectively, wherein an ultrasound beam scans a certain section for one frame of data, and then the beam is shifted slightly by a width smaller than a beam thickness to san the next section for one frame of data in the same manner as above. Either scanning technique permits any location, which is arbitrarily selected in the scanned three-dimensional space, to be scanned during a period of one heartbeat. This volume scan makes it possible ultimately to calculate corrected velocities in each section, thus making it possible ultimately to display the pulsatility in the three-dimensional manner.

The scanning techniques shown in FIGS. 16(b) and 17(b) are superior in respect of accuracy for calculating corrected velocities, since each section to be scanned is stationary during a period of one heartbeat. On the other hand, the techniques shown in FIGS. 16(c) and 17(c) are advantageous in that corrected velocities can be calculated specially with fineness, because sections to be scanned are consecutively located.

The scan controller 23 of the transmitter 2A (refer to FIG. 15) can realize these scanning technique, in which the controller 23 is operated to control scanning toward each section to be scanned. Sequences for such scan control are exemplified in FIGS. 18(a) to 18(c).

Figure 18A:
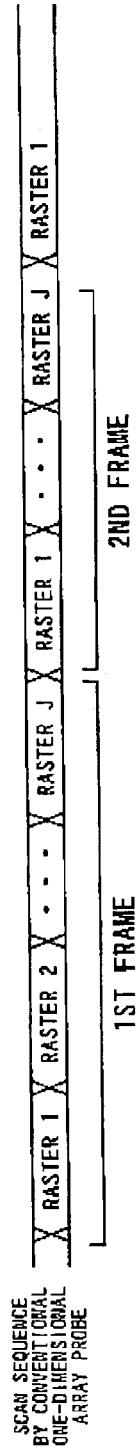
FIGS. 18(a) to 18(c) are examples of control sequences for the volume scan.

Of these, FIG. 18(a) shows an example of a scan sequence used for a conventional one-dimensional array type of probe. This sequence explains that a plurality of rasters composing the same section to be scanned (refer to "raster 1, raster 2, . . . , raster J" in FIG. 18(a)) are repeatedly scanned for each frame of data (refer to "$1^{st}$ frame, $2^{nd}$ frame, . . . " in FIG. 18(a)).

Figure 18B:
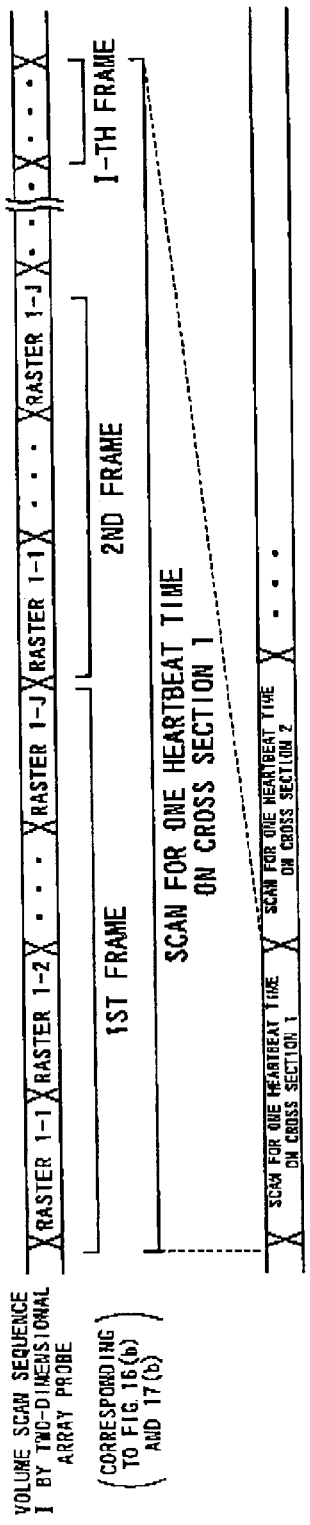
Figure 18C:
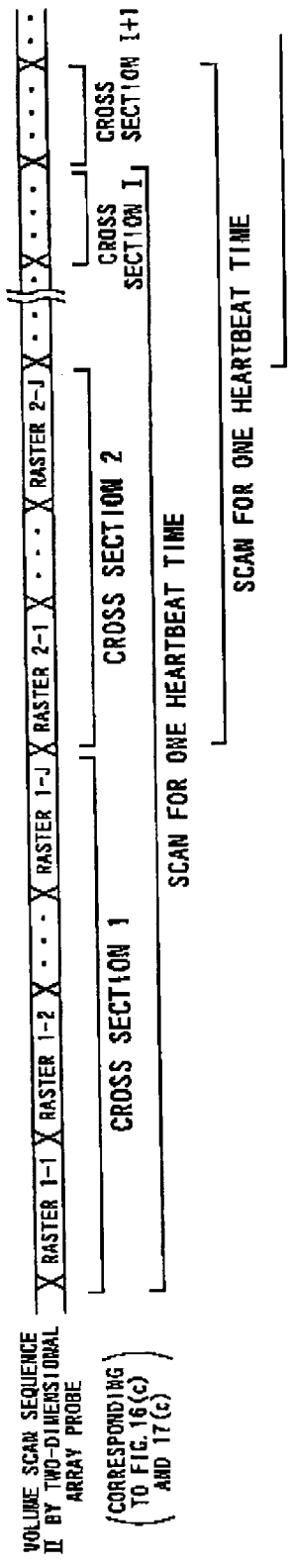

In contrast, FIGS. 18(b) and 18(c) explain examples of scan sequences directed to the volume scan performed with the aid of the two-dimensional array type of probe according to the present embodiment.

Of these examples, the sequence exemplified in FIG. 18(b) is directed to the foregoing scanning techniques shown in FIG. 16(b) and FIG. 17(b). Practically, as shown in FIG. 18(b), with respect to a certain one section located within a spatial region to be subjected to the volume scan (refer to "section 1" in FIG. 18(b)), a plurality of rasters composing the section (refer to "raster 1-1 (meaning that a raster 1 on the section 1), raster 1-2, . . . , raster 1-J" in FIG. 18(b)) are scanned to produce data for one frame, and then the same scanning to the plurality of rasters of the same section are repeatedly performed I-times (i.e., for I-pieces of frames), which leads to acquisition during a period of one heartbeat. After completing the scanning at the foregoing section, the ultrasound beam is controlled to scan the next section (refer to "section 2" in FIG. 18(b)) is shifted stepwise from the previous one by a width equal to a beam thickness. At the section 2, the scanning is also performed similarly to the above during a period of one heartbeat. The same scanning manner is repeatedly applied to each of the remaining sections located in the spatial region realized by the volume scan.

In addition, the sequence exemplified in FIG. 18(c) is directed to the foregoing scanning techniques shown in FIG. 16(c) and FIG. 17(c). Practically, as shown in FIG. 18(c), first of all, a plurality of rasters (refer to "raster 1-1, raster 1-2, . . . , raster 1-J" in FIG. 18(c)) constituting a certain one section located within a volume region to be scanned (refer to "section 1" in FIG. 18(c)) undergo scanning for one frame of data by an ultrasound beam. Then, the ultrasound beam is controlled to scan the next section (refer to "section 2" in FIG. 18(c)) slightly shifted from the previous one by a width less than a beam thickness (for instance, a width equal to 1/I of a beam thickness). The next section (i.e., "section 2") is then subjected to scanning for one frame of data in the same manner as above. Hereafter, as sections to be scanned are shifted little by little, the scanning for "section 3, . . . , section 1, section I+1, . . . " is conducted consecutively in turn. A period of time for one heartbeat is required to scan I-piece sections. The data acquired from the sections ranging from the section 1 to the section I is used to calculate corrected velocities, so that one section on which the corrected velocities are mapped is produced. After a delay of time for one frame, the data acquired from the sections ranging from the section 2 and the section I+1 is used to calculate corrected velocities. Hence, the next section on which the corrected velocities are mapped is produced. Hereafter, in the same manner as above, other sections on each of which corrected velocities are mapped are consecutively produced with a delay of time for one frame left therebetween, whereby the plural sections mutually adjacently allocated in time are produced.

For performing the volume scan, a parallel simultaneous reception technique may be used which enables simultaneous reception along a plurality of directions in response to one time of transmission for scanning a section. For instance, this technique can be applied to simultaneous scans toward a plurality of sections, providing various advantages including a shortened time for scanning a volume region. As long as each section is scanned during a period of time for one heartbeat, the parallel simultaneous reception technique can be implemented into various types of scanning techniques.

Because exemplified in the present embodiment is an electronic scan that uses the two-dimensional array probe 7, advantages derived therefrom will now be explained compared to the other scanning methods (that use a one-dimensional array type of probe).

FIG. 19(a) illustrates a conventionally known scan technique, called hand scan, by using an electronic scan probe (one-dimensional array type of probe) with a one-dimensionally arrayed transducer. An operator holds the probe by hand, and moves the probe in a perpendicular direction to the sections to be scanned every time each section has been scanned in a usual scanning manner. As stated before, a consecutive operation to positionally shift sections to be scanned with data acquired during a period of time for one heartbeat involves a heavier difficulty, thus being not practical.

Further, FIG. 19(a) is another illustration explaining how to scan each section, which has been known as well. That is, a conventional electronic scan probe (one-dimensional array type of probe) with a one-dimensionally arrayed transducer is mounted to a known probe-moving unit with a guide mechanism and rotation mechanism which use guide rods. The probe-moving unit is operated to slowly move the probe so that each section is scanned during a period of time for one heartbeat for acquisition of volume data. This unit allows each section to scanned over a period of time for one heartbeat. However, the unit should be large-scale and the operations between scans and the prove movements should be in synchronism with each other, thus complicating the control, thus being not practical as well, as explained about FIG. 19(a).

In contrast, FIG. 19(c) is an illustration to explain an electronic scan with the use of the two-dimensional array type of probe 7 according to the present embodiment. When using this scan technique, it is sufficient for an operator to only fix the probe 7 on a desired region of a subject to be examined. This operation makes it possible that volume data is automatically acquired and depicted with higher accuracy and the pulsatility is three-dimensionally depicted with precision in a simpler manner.

Based on the data acquired by the two-dimensional array type of probe 7, velocities are corrected. For example, maximum velocities can be employed as the corrected velocities, whereby it is easier to perform three-dimensional reconstruction. The velocity corrector 42 responsible for the foregoing correction based on the maximum velocities is exemplified in its construction in FIG. 20.

Figure 20:
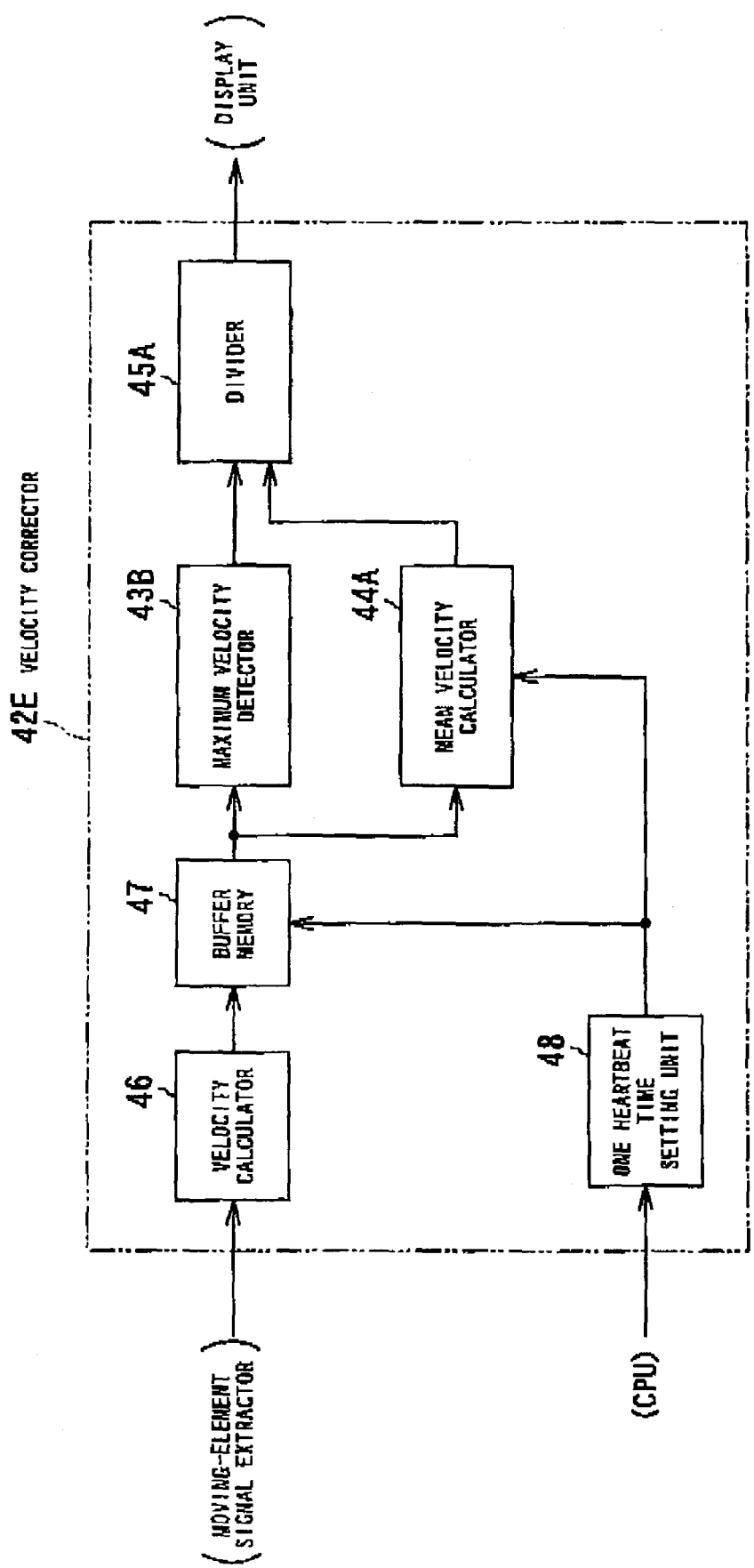
FIG. 20 is a schematic block diagram practically exemplifying a velocity corrector that adopts a maximum velocity as a velocity characterizing the pulsation.
Figure 21:
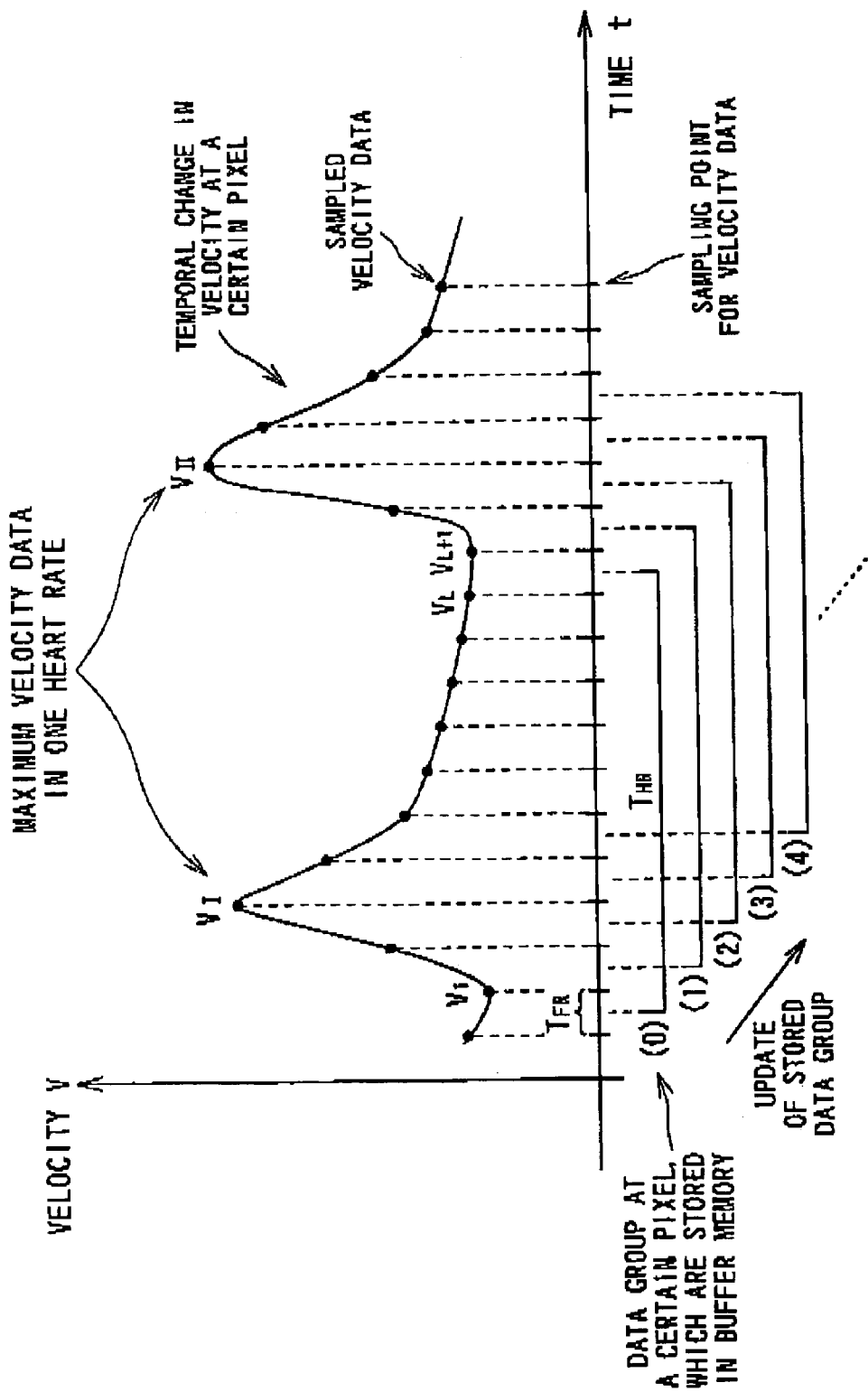
FIG. 21 is a time-velocity chart depicting the operation of velocity corrector shown in FIG. 20.

A velocity corrector 42E shown in FIG. 20 comprises, in addition to the velocity calculator 46, buffer memory 47, mean velocity calculator 44A, divider 45A, and one-heart-beat-time setting unit 48, as similarly to FIG. 3, a maximum velocity detector 43B serving as the pulsation-characterizing velocity calculator. FIG. 21 exemplifies the operation at the maximum velocity detector 43B.

In the similar way to that in FIGS. 4(*a*) and 4(*b*), changes in velocity V over time t at a certain one pixel are shown in FIG. 21. In FIG. 21, $T_{FR}$ indicates a sampling time for velocity data ($T_{FR}$=1/the number of frames); $T_{HR}$ indicates a period of time for one heartbeat; $V_1, \ldots, V_I, \ldots, V_L$, $V_{L+1}, \ldots, V_{II} \ldots$ indicate velocity data sampled per sampling time $T_{FR}$ at a certain pixel; a data group (0) indicates a group of velocity data ($V_1, V_2, \ldots, V_L$) stored in the buffer memory 47 during one heartbeat time $T_{HR}$ at a certain time instant; and a data group (1) indicates a group of velocity ($V_2, \ldots, V_{L+1}$) stored one frame later than a time phase at which the data group (0) is obtained. The remaining data groups (2), (3), (4) . . . are also obtained in the same way.

In buffer memory 47, the data update is carried out in such that the oldest data in the data group, that is, velocity data $V_1$, is removed, while the latest data, that is, $V_{L+1}$, is added. This updating technique is repeated at intervals in turn.

In response to the operations in the buffer memory 47, the maximum velocity detector 43B operates to read out a maximum velocity from each of the groups of velocity data. Practically, in the case of the example shown in FIG. 21, a velocity $V_I$ is read out of each of the data groups (0) to (2) and a velocity $V_{II}$ is read out of each of the data groups (3) and (4). The read maximum velocities are sent in sequence to the divider 25 45A. Because each of the groups of velocity data consists of velocities acquired during one heartbeat time $T_{HR}$, every data group always includes data of a maximum velocity appearing during a period of tome for one heartbeat. In addition, each of the groups of velocity data to be stored is updated at any time, whereby the latest velocity is always new.

In parallel, as described before, the mean velocity calculator 44A is engaged in the consecutive calculation of each mean value $<V>_0$ ($<V>_1, <V>_3, <V>_4, \ldots$) of each of the groups of velocities, whereby the resultant values are routed to the divider 45A.

Thus, the divider 45A receives both of a maximum velocity $V_I$ ($V_{II}$, and others) from the maximum velocity detector 43B and a mean velocity $<V>_0$ ($<V>_1, <V>_3, <V>_4$, and others) from the mean velocity calculator 44A, and then calculates consecutively a corrected velocity $V_{cmp0}$ ($V_{cmp1}$, $V_{cmp2}$, $V_{cmp3}$, and others) using themes values that have been received, on the basis of the equations expressed as follows:

$$V_{cmp0} = V_I/<V>_0$$

$$V_{cmp1} = V_I/<V>_1$$

$$V_{cmp2} = V_{II}/<V>_2$$

$$V_{cmp3} = V_{II}/<V>_3$$

In these equations, in lieu of mean velocities that are the denominators, the absolute values of the mean velocities may be adopted, whereby the corrected velocities can be calculated on the following equations.

$$V_{cmp0} = V_I/|<V>_0|$$

$$V_{cmp1} = V_I/|<V>_1|$$

$$V_{cmp2} = V_{II}/|<V>_2|$$

$$V_{cmp3} = V_{II}/|<V>_3|$$

Thus, the data of corrected velocities that have been oriented can be obtained, where each of which is directionally separated on the positive and negative signs of instantaneous velocities that are numerators.

In addition, corrected velocities may be obtained as their absolute values by the following equations:

$$V_{cmp0} = |V_I/<V>_0|$$

$$V_{cmp1} = |V_I/<V>_1|$$

$$V_{cmp2} = |V_{II}/<V>_2|$$

$$V_{cmp3} = |V_{II}/<V>_3|$$

so that the obtained values indicate only magnitudes of the corrected velocities. This calculation is identical to that previously shown on FIG. 3.

This calculation enables the display of only maximum velocities that have been corrected. For instance, when applied to the foregoing example shown in FIG. 5, the artery is always depicted in yellow showing faster velocities, while the portal vein and vein are always depicted in red showing slower velocities. Therefore, an image, which is like a still image, can be displayed. In general, if pieces of information independent of changes in the cardiac time phase is used as pieces of information in relation to the pulsatility, an image, which can be seen like a still image, is displayed. This kind of image is especially effective when it is desired to observe still images, preserve data of still images, produce three-dimensional images, and others.

The maximum velocities that have been corrected are constantly updated in real time, without being frozen. Thus, even if a blood vessel is slightly moved in the subject's body due to, for example, a soft breathing, the blood vessel on an image can also be moved and depicted, still providing effective information that tracks the vessel. Accordingly, using such maximum velocity data that has been corrected makes it possible to provide pulsatile images that are excellent in visibility, preservation, and real-time performance, and suitable for constituting three-dimensional images. As a result, a diagnostic performance can be improved further.

The data of corrected velocities calculated by the velocity corrector 42B is then sent to the display unit 8, as described before (refer to FIGS. 15 and 20). The display unit 8 has, as described in FIG. 15, the three-dimensional color image memory 81 and the three-dimensional tomographic image memory 82, both of which serves as image memories and are able store three-dimensional data therein. The foregoing data of corrected velocities is thus stored in the three-dimensional color image memory 81, while tomographic image data two-dimensionally or three-dimensionally acquired and processed is stored in the three-dimensional tomographic image memory 82.

When the foregoing volume scan to acquire volume data is completed, the three-dimensional data of corrected velocities stored in the three-dimensional color image memory 81 and the two-dimensional or thee-dimensional tomographic image data stored in the three-dimensional tomographic image memory 82 are both read out. The read-out data are then subject to display processing according to a format specified and inputted by an operator through a not-shown operation panel, with the result that a three-dimensional image is depicted on the monitor 84 in cooperation with the DSC 83. Examples of display of such three-dimensional images are shown in FIGS. 22(*a*) and 22(*b*).

Figure 22:
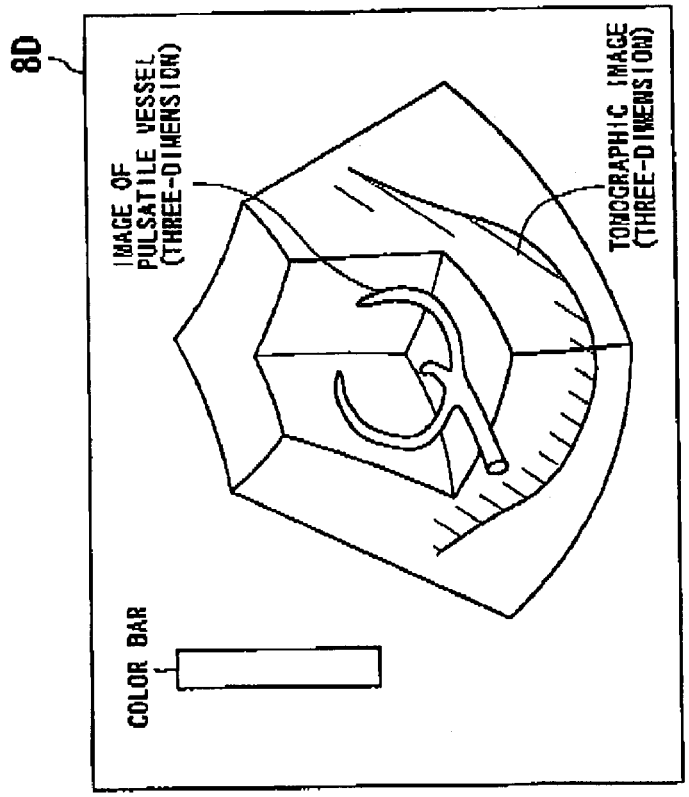
FIGS. 22(a) and 22(b) are views illustrating display examples of three-dimensional images.
Figure 22:
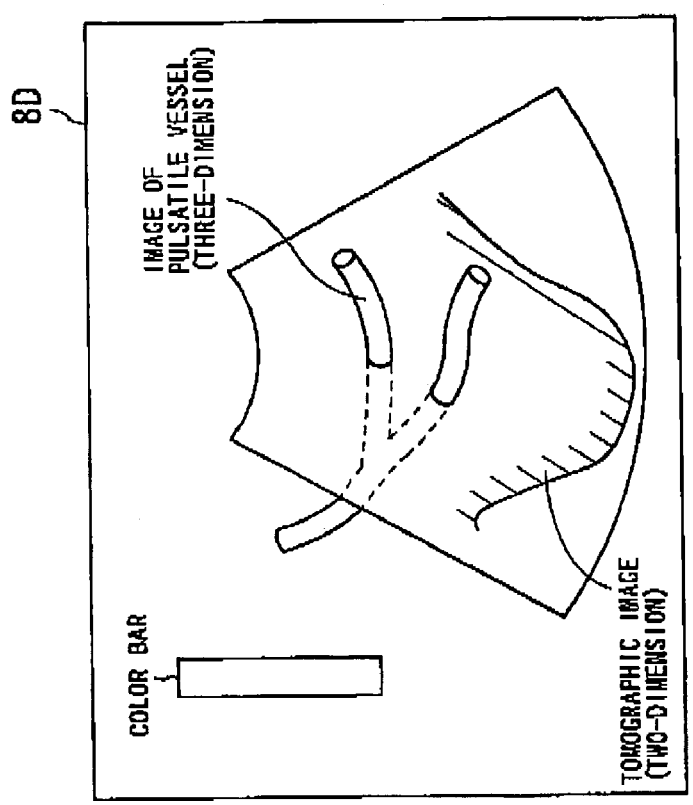

FIG. 22(*a*) illustrates an image formed by combining a two-dimensional topographic image with a three-dimensional pulsating vessel image, whilst FIG. 22(*b*) illustrates an image formed by combining a three-dimensional tomographic image with a three-dimensional pulsating vessel image.

Accordingly, the above characteristics of image display can be applied to proper use originated from necessity. A pulsating vessel can therefore be displayed three-dimensionally, during which time a user is allowed to identify a desired position or observe a lesion on a topographic image. This makes it possible that both of the artery and the vein are observed with improved vessel continuity, greater visibility, convenience, and clearer distinction, whereby the efficiency and accuracy of each examination can be improved to a greater extent.

As explained above, the foregoing first and second embodiments permit the pulsation of blood vessels to be tracked, thus being in principle depicted distinguishably between the artery and the vein. However, it is clear that there is no one-to-one correspondence as to the pulsatility between the artery and vein, and it is conceivable that some exceptions may occur.

For example, an inferior vena cava indicates to some extent the pulsatility. In such a case, even a vein may provide an image in which the pulsatility appears to a small extent. In contrast, a Doppler image shown in FIG. 23 may be provided, where there are smaller changes in velocity compared to a mean velocity over one heartbeat, even though a blood flow with a tumor exhibits the pulsatility. In such a case, there is a possibility that the image does not provide a clear pulsatility of a blood vessel to be observed, despite the real existence of the pulsation thereof.

Countermeasures for improving the above situation will now be described on examples preferably shown in FIGS. 24 and 25.

In the case of such examples, first of all, the calculation for velocity at individual pixels is carried out by the CFM processor to obtain velocities at the pixels, like the conventional. Then, as shown in FIG. 24, a maker is placed on a pulsatile image to specify a certain pixel. Responsively to this specification, temporal changes in velocity at the specified pixel (that is, a velocity-time chart) are depicted together with the pulsatile image.

This display technique allows spectrum Doppler data to be obtained from the same scanned data as those used for display the pulsatility, thus preventing the number of frames from being lowered. In contrast, the conventional parallel display of CFM images and spectrum Doppler data require to be scanned separately and dedicatedly from each other, resulting in that the number of frames which can be used for CFM images is decreased down to half of the frames. The advantage of keeping the number of frames, which can be obtained by the present embodiment, is thus strictly significant if it is desired that an ejection period be securely tracked for displaying the pulsatility. Moreover, another advantage of the present embodiment is that temporal changes in velocities detected at a plurality of positions are displayable, although the conventional parallel display of CFM images and spectrum Doppler data allows Doppler spectrum data to be displayed at only one position. Thus, the present embodiment is able to provide a remarkably improved usage. Of course, in the present embodiment, Doppler spectrum data at a plurality of positions can be displayed in real time in synchronism with displaying pulsatile images. Additionally, only a chart showing velocities versus time or only pulsatile images can be frozen.

A modification is that a marker used in the present embodiment is variable in its size. Thus, spatial averaging of data enclosed by the size-changeable marker is able to stabilize velocity data that will be produced. In the present embodiment, plotting a velocity at each frame forms charts showing the relationship between velocities versus time, which are exemplified in FIGS. 25(*a*) to 25(*b*). As shown therein, how to plot velocities can be changed, For instance, a velocity obtained at each frame is plotted with the use of a dot. Alternatively, such dots can be connected with polygonal lines or a curved line. Another modification is that an electrocardiographic gating technique is used to obtain velocities as the cardiac time phase is shifted gradually and velocities obtained during several heartbeats are overlaid one on another, thus providing a chart with closer intervals of time. Still, another modification is concerned with the calculation of velocities, in which a mean velocity at each pixel, which is usually obtained for only the display, is combined with the dispersion of a velocity at the pixel, in order to obtain a pseudo maximum velocity for display. Moreover, the foregoing embodiment is suitable for real-time display, but this is not a definite list. By way of example, the display of the pulsatility may be frozen, before a velocity-time chart at a specified pixel is displayed, if velocity data is once stored in a memory.

The above various modifications will upgrade images that depict pulsatile flows, making it possible to detect pulsatility in a more sure fashion, thus further improving a diagnostic performance.

The foregoing pulsatile flow display can be applied to the following first to third examples.

1) The first application example is concerned with combining the foregoing pulsatile flow display with a known broad-band transmission technique (refer to, for example, Japanese Patent Laid-open (KOKAI) publications Nos. 2000-342586 and 2001-269344). This "broad-band transmission" technique, which is carried out under the power Doppler mode, is a way of transmitting an ultrasound pulse consisting of one or two burst waves, instead of transmitting an ultrasound pulse consisting of four to eight burst waves. The one or two burst waves are equivalent in the number of burst waves to that under the B-mode, thus providing a broad-band ultrasound pulse. This "broad-band transmission" technique is able to provide range discrimination essentially equivalent to the B-mode (for example, refer to a Japanese Patent Laid-open (KOKAI) Publication No.2000-342586).

One example of the broad-band ultrasound pulse is an ultrasound pulse of which number of burst waves is less than three. By using this ultrasound pulse, it becomes possible to obtain blood flow images of high spatial resolution with no or almost no blooming, so that diagnostic performance is further improved (refer to a Japanese Patent Laid-open (KOKAI) Publication No. 2000-342586, for example). Computing the reciprocal number of a transmission frequency of a transmission ultrasound pulse produces one cycle of the transmission pulse. An ultrasound pulse of which duration is equal to one cycle of a transmission pulse is called a "pulse of one burst wave" and an ultrasound pulse of which duration is equal to two cycles of a transmission pulse is called a "pulse of two burst waves." Thus, an ultrasound pulse of which duration is equal to M-cycles of a transmission pulse is called a "pulse of M-piece burst waves." One burst waves, two burst waves, . . . , M-piece burst waves are called the number of burst waves.

Accordingly, the present application example will provide a further improved resolution performance, in addition to the effects derived from the foregoing pulsatile flow display.

2) The second application example concerns an improved way of calculating the foregoing reference velocity.

FIG. 26 exemplifies temporal changes in velocity (i.e., changes in velocity in the frame direction) at a certain one pixel on a colored map providing a blood flow image, which is adopted to explain a formula for calculating the foregoing corrected velocities. In this example, an example is provided without loosing the generality such that the reference velocity is given as a mean of absolute values of velocities over one heartbeat time and corrected velocities are given as "corrected velocities=absolute values of instantaneous velocities/a mean of absolute values of velocities acquired over one heartbeat time." As described above, the corrected velocities are obtained by dividing velocity data by a velocity at the same pixel, thereby dissolving the drawback from the Doppler angle dependency. Thus the pulsatility at a blood vessel can be detected more clearly. In this case, normally, a mean is calculated through one time of averaging over all instantaneous velocities acquired over one heartbeat time.

Figure 27:
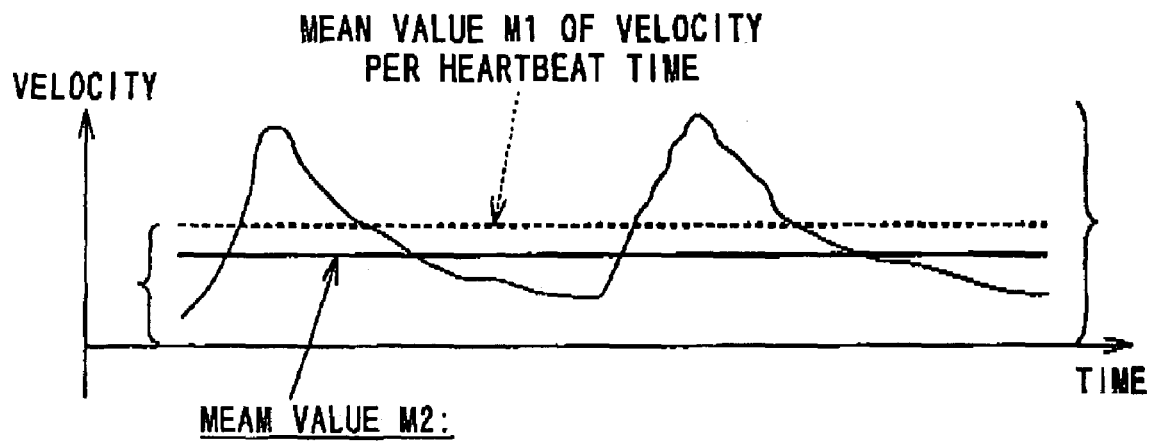
FIG. 27 illustrates a mean value of velocity obtained when a double averaging technique is applied to an artery.
Figure 28:
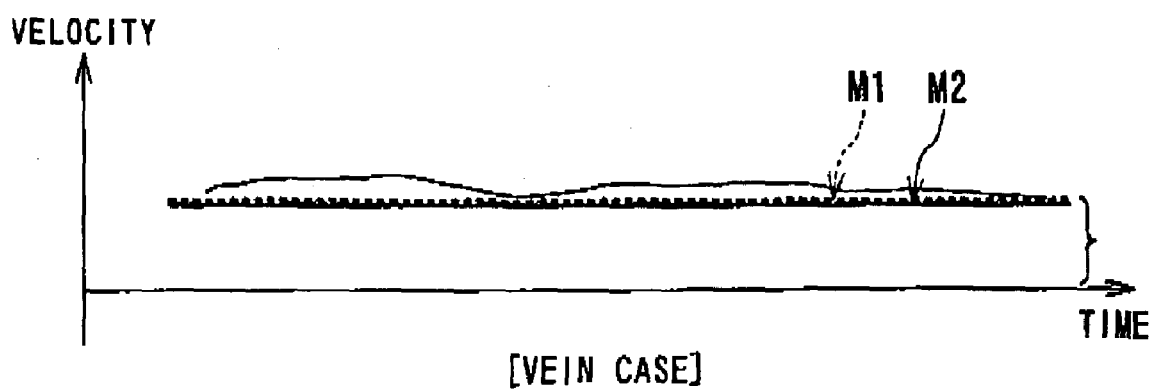
FIG. 28 illustrates a mean value of velocity obtained when a double averaging technique is applied to a vein.

In addition to the foregoing one-time averaging technique, a two-time averaging technique can be provided as the technique for calculating a mean according to the present application example, which is shown in FIG. 27 (for the artery) and in FIG. 28 (for the vein). The two-time averaging technique is used to average all instantaneous velocities acquired over one heartbeat time so that a mean M1 is figured out, to average only instantaneous velocities equal to or less than a value (=M1×Th-value) obtained by multiplying the mean M1 by a predetermined value (corresponding to Th-value; for instance, Th-value=1+α) so that a mean M2 is figured out through the second averaging, and to adopt the mean M2 for the mean M1 as the denominator in the foregoing calculating formula. In other words, instantaneous velocities larger than the value of M1×Th-value are excluded from the calculation of the mean M2.

This two-time averaging technique is advantages as follows. 1) In the artery shown in FIG. 27, compared to the mean M1 obtained from the one-time averaging technique, the pulsatility is enhanced correspondingly to a decrease in the mean M2 derived from the second averaging calculation. In contrast, in the case of the vein shown in FIG. 28, there is almost no difference between the means M1 and M2, so that the vein is depicted as a non-pulsatile flow. 2) The mean M2 figured out by the second averaging is sensuously more closer to a mean obtained thorough manual tracing on the image shown in FIG. 27, thus being easier to understand. 3) Even only an ejection period has been subjected to the detection, the pulsatility is easier to display. Therefore, the artery and vein are more clearly distinguished one from the other, whereby a diagnostic performance can be improved more.

3) The third application example is directed to a display mode, in which both of the foregoing pulsatile flow display and a known power display are carried out by mixture.

In the case that an organ is moved by breathing, heartbeats, or others, or a blood vessel to be observed is a peripheral blood vessel or a blood vessel with the large Doppler angle, it happens that the blood flow signal may not be detected temporarily or at some cardiac time phases. Resultantly, the reference velocity may not be determined, which make it impossible to correct velocities of a moving element.

To be specific, in cases where an organ moves, any one pixel on a blood vessel may not be present at the same location during one heartbeat time. Hence, all the velocity data of a moving element which should be gathered during one heartbeat time are not always fully acquired, thereby lacking data.

In addition, in the case of a peripheral blood vessel, a velocity of blood is slow, so that a possible Doppler signal frequency to be detected becomes lower. In the case of a blood vessel having a larger Doppler angle, a Doppler signal frequency to be detected is also obliged to be lower due to its angle dependency. In such cases, an MTI filter operates to eliminate a signal of which Doppler frequency is lower. This means that, for example, it is possible to detect Doppler signals during an ejection period at the artery, while it is difficult to fully detect Doppler signals during a diastole thereat. If such an occasion occurs, it is impossible to prepare for all velocity data of a moving element during one heartbeat time, thus lacking data.

The present application example is to cope with such a situation. For this purpose, this example is configured such that the reference velocity can be determined even when velocity data of a moving element lacks to some extent. Hereinafter, this will be described about one pixel on an image.

Figure 29:
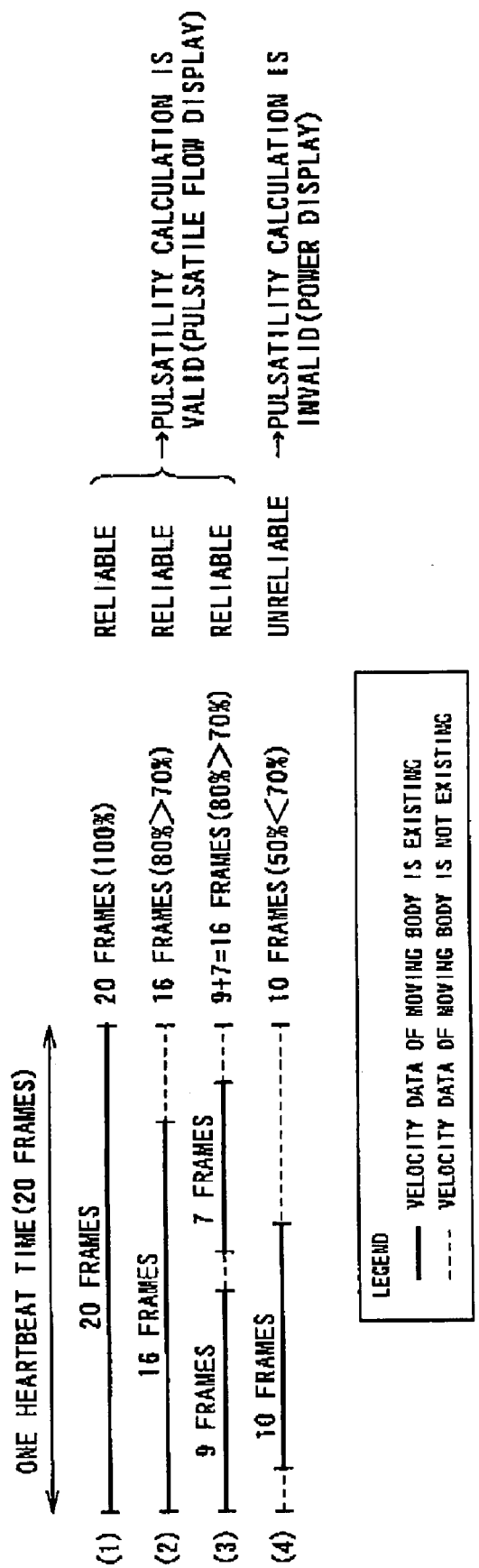
FIG. 29 explains how to use an effective frame rate of velocity data during a period of time of one heartbeat to determine whether the calculation of the pulsatility is valid or invalid.

As shown in FIG. 29, it can be assumed that there are 20 frames in one heartbeat time. By way of example, if velocities of a moving element can be detected in 70% or more of all the 20 frames, i.e., in 14 frames or more, it can thus be determined that a reference velocity calculated on velocity data of those frames is reliable. If such a determination can be done, a reference velocity is calculated accordingly. Those 14 frames may be consecutive (refer to (1) and (2) in FIG. 29) or intermittent (refer to (3) in FIG. 29). Using the calculated reference velocity, moving velocities detected from a moving element are then corrected for pulsatile display at pixels subjected to the velocity correction on each of the frames that have contributed to calculating the reference velocity.

In contrast, if velocities of a moving element can be detected only in frames less than 14 frames among the 20 frames, the determination can be made such that a reference velocity calculated on velocity data of those frames is unreliable. If such a determination can be done, a reference velocity will not be calculated, thus the velocity correction being not performed (refer to (4) in FIG. 29). In this case, however, signals are still detected from blood flowing in a region to be scanned. Therefore, to show that there is blood flow in the region, the display on the ordinary power display mode is carried out at pixels in frames that have been related to the velocity detection. However, neither the pulsatile display nor the power display is applied to pixels at which velocities of a moving element have not been detected.

As a result of it, as shown in FIG. 30(*a*), both of the pulsatile display and the power display are conducted by mixture (hereafter, this display mode is referred to as "pulsatile flow/power mix display"). This pulsatile flow/power mix display allows all the detected blood vessels to be depicted, while still maintaining the display of the pulsatility of blood vessels that have been subjected to the velocity correction. It is therefore possible to obtain higher detectability of blood vessels and to display the pulsatility of the blood vessels with higher detectability, thus improving a diagnostic performance to a greater extent.

In this pulsatile flow/power mix display mode, for enhanced visibility, it is preferred that a pulsatile flow image and a power image are both depicted in colors. Color bars for such display are exemplified in FIGS. 30(b) and 30(c), in which two color bars are placed together; one is for corrected velocities (i.e., for a pulsatile flow image) and the other is for a power image.

Figures 10A, 10B, 10C, 10D, 10E:
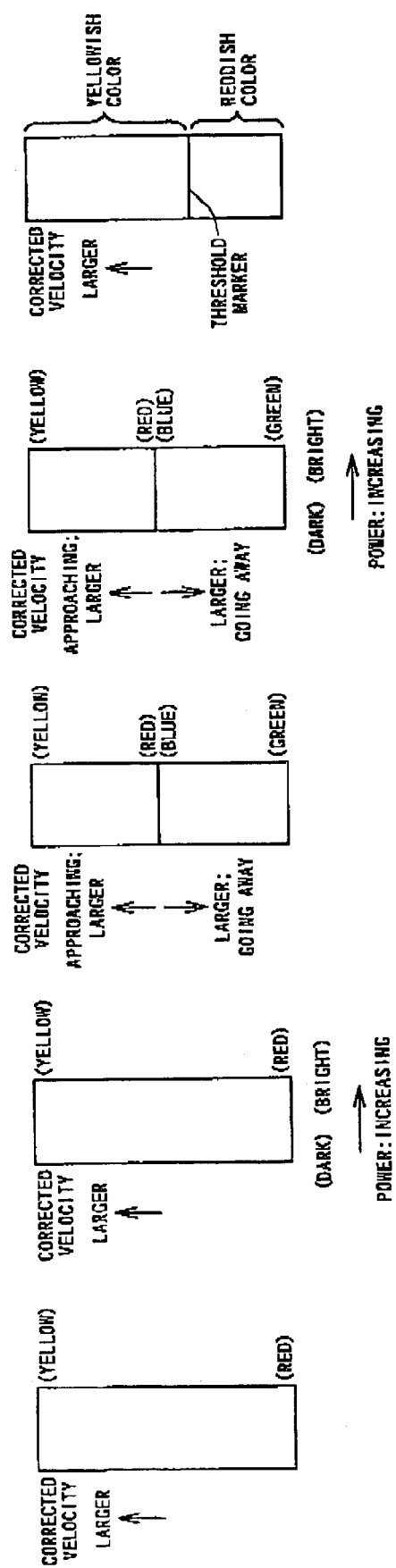
FIGS. 10(a) to 10(e) illustrate examples displaying color bars.
Figure 30A:
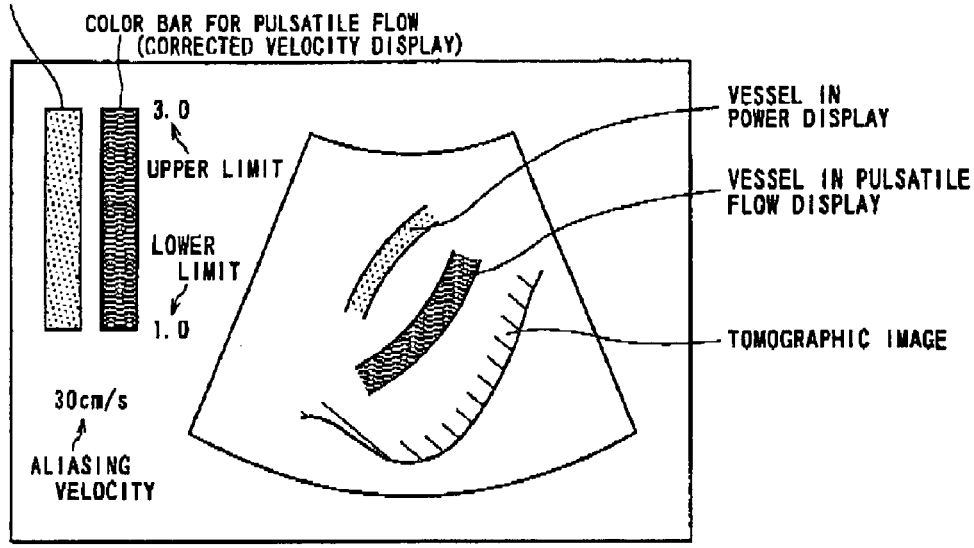
FIGS. 30(a) to 30(d) are views exemplifying display of both the pulsatility and power in a mixed manner.
Figures 30B, 30C:
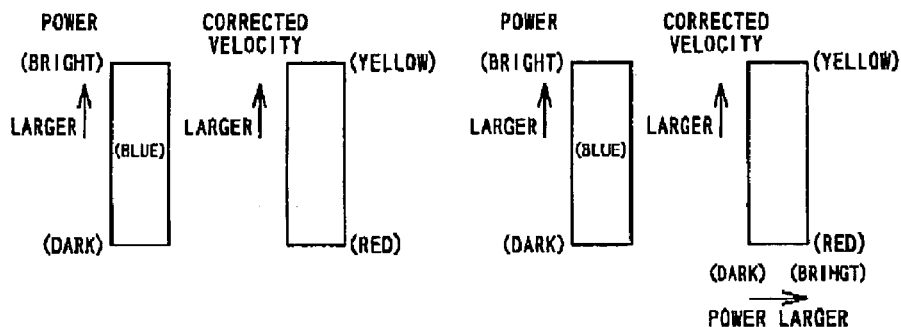

The example in FIG. 30(b) shows a combination of the color bar for corrected velocities, which has been shown in FIG. 10(a), and a color bar for an ordinary power image. The example in FIG. 30(c) shows a combination of the color bar for corrected velocities, which has been shown in FIG. 10(b), and a color bar for an ordinary power image. In each of the two cases shown in FIGS. 30(b) and 30(c), the corrected velocities and power values are colored differently from each other. Thus, a clear distinction is provided between a pulsatile flow image and a power image, and a clear distinctiveness is given to degrees of the pulsation appearing in a pulsed flow. Both of detectability and a diagnostic performance will be upgraded largely.

Furthermore, an upper limit and a lower limit accompany the color bar for corrected velocities shown in FIG. 30(a) previously described. This way of attaching the limit values makes it easier to read out a degree of the pulsation from the color bar.

Figure 30D:
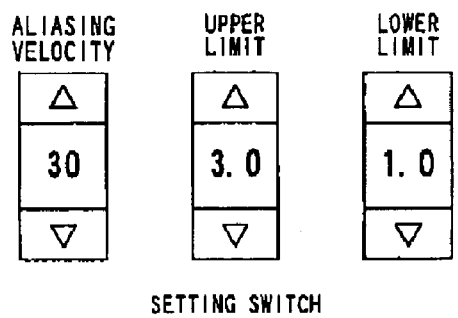

In addition, as shown in FIG. 30(d), a setting switch can be provided on a not-shown operation panel in order to allow an operator to give desired values to the upper and lower limits for corrected velocities, whereby the visibility for the pulsation can be enhanced. As a further modification, an aliasing velocity can be placed on the image shown in FIG. 30(a), while a setting switch is installed on a not-shown operation panel as shown in FIG. 30(d). This configuration makes it possible that, with viewing the image shown in FIG. 30(a), an operator sets a properly chosen aliasing velocity, which is able to elevate a depiction performance for the pulsation.

As has been described above, the present application examples are able to not only raise the detectability for blood flow and its pulsatility but also enhance the visibility for the pulsation. This is helpful for a greatly improved diagnostic performance.

The present invention is not limited to the foregoing embodiments that are typically shown and various modifications and alterations may occur to one skilled in the art based on contents written in the claims, without departing from the spirit of the present invention. These modifications and alterations pertain to the claim(s) of the present invention.

What is claimed is:

1. An ultrasonic diagnosis apparatus comprising:
   means for scanning a subject to be examined while transmitting and receiving an ultrasound pulse to and from the subject, whereby reception signals are obtained at each pixel of a scanned portion of the subject from the received ultrasound pulse;
   means for obtaining, every pixel, in sequence a plurality of velocities of a moving element that is in motion within the subject on the basis of the reception signals obtained during a predetermined period of time corresponding to one heartbeat of the subject, the velocities being updated in real time;
   means for computing a reference velocity based on the plurality of velocities obtained by the means for obtaining during the predetermined period of time and for correcting velocity information based on the velocities of the moving element using the reference velocity, the velocity information indicating a characteristic of the heartbeat of the subject; and
   means for displaying the corrected velocity data as an image so that the corrected velocity information is updated in display a plurality of times during the predetermined period of time.

2. An ultrasonic diagnosis apparatus comprising:
   means for three-dimensionally scanning each of sections of a subject to be examined a plurality of times during a period of time corresponding to one heartbeat of the subject while transmitting and receiving an ultrasound pulse to and from the subject, whereby reception signals are obtained at each pixel of the sections of the subject from the received ultrasound pulse;
   means for obtaining, every pixel, velocities of a moving element that is in motion within the subject on the basis of the reception signals obtained during a predetermined period of time based on the one heartbeat of the subject, the velocities being updated in real time;
   means for computing a reference velocity based on the plurality of velocities obtained by the means for obtaining during the predetermined period of time and for correcting velocity information based on the velocities of the moving element using the reference velocity, the velocity information indicating a characteristic of the heartbeat of the subject; and
   means for displaying a three-dimensional image based on the corrected velocity information so that the image in display is updated a plurality of times during the predetermined period of time.

3. An ultrasonic diagnosis apparatus comprising:
   a scanning unit configured to scan a subject to be examined while transmitting and receiving an ultrasound pulse to and from the subject, whereby reception signals are obtained at each pixel of a scanned portion of the subject from the received ultrasound pulse;
   an obtaining unit obtaining, every pixel, a plurality of velocities of a moving element that is motion within the subject on the basis of the reception signals obtained during a redetermined period of time corresponding to one heartbeat of the subject, the velocities being updated in real time;
   a processing unit computing a reference velocity based on the plurality of velocities obtained by the obtaining unit during the predetermined period of time and correcting velocity information based on the velocities of the moving element using the reference velocity, the velocity information indicating a characteristic of the heartbeat of the subject; and
   a displaying unit configured to display the corrected velocity data as an image so that the corrected velocity information is updated in display a plurality of times during the predetermined period of time.

4. The ultrasonic diagnosis apparatus according to claim 3, wherein the reference velocity is at least one selected from a group of values consisting of:
   1) a mean of the velocities acquired during the predetermined period of time or an absolute value of the mean thereof, 2) a mean of absolute values of velocities acquired during the predetermined period of time,
3) an RMS (Root Mean Squire Value) value of the velocities acquired during the predetermined period of time,
4) a value or an absolute value thereof, which is calculated by applying any one of an FIR (Finite Impulse Response) filter, IIR (Infinite Impulse Response) filter, and a non-linear filter to velocities acquired during the predetermined period of time or absolute values of the velocities, and
5) a vectorial mean of the velocities acquired from the predetermined period of time or an absolute value of the vectorial mean.

5. The ultrasonic diagnosis apparatus according to claim 4, wherein the processing unit comprises means for re-averaging the velocities of the moving element which are equal to or smaller than a value produced by multiplying the average by "1+α" (α≧0) after the average and for setting to the reference velocity another mean obtained by the re-averaging.

6. The ultrasonic diagnosis apparatus according to claim 3, wherein the processing unit comprises at least one of:
  1) means for dividing the velocities of the moving element by the reference velocity, and
  2) means for converting the velocities of the moving element to values relative to the reference velocity.

7. The ultrasonic diagnosis apparatus according to claim 3, wherein the processing unit includes at least one of means for correcting aliasing resultant from a sampling theorem for the velocities obtained by the obtaining unit and means for moderating temporal changes in the corrected velocity information obtained by the processing unit.

8. The ultrasonic diagnosis apparatus according to claim 3, wherein the scanning unit is configured to scan one section of the subject at the number of frames larger than a value indicated by an inverse number of a period of time corresponding to an ejection period of cardiac pulsation of the subject, the section serving as the scanned portion of the subject.

9. The ultrasonic diagnosis apparatus according to claim 3, wherein the display unit is configured to display a two-dimensional image of the corrected velocity information obtained by the processing unit.

10. The ultrasonic diagnosis apparatus according to claim 3, further comprising a unit configured to obtain a tomographic image of a section of the subject, the section being the scanned portion and the tomographic image being either of a two-dimensional image or a three-dimensional image,
  wherein the display unit has at least one of means for displaying on the same monitor the tomographic image and the image of data obtained by the processing unit and means for displaying on the tomographic image the image of data obtained by the processing unit in a superposition manner.

11. The ultrasonic diagnosis apparatus according to claim 3, wherein the displaying unit comprises at least one of:
  means for displaying in colors the image of data obtained by the processing unit,
  means for displaying pieces of information formed by combining the data obtained by the processing unit and power information of scattering echoes from the moving element within the subject,
  means for displaying a color bar mapped not only by a hue indicative of a lower velocity when magnitudes of the data obtained by the processing unit are nearly equal to or less than the reference velocity but also by other hues indicative of higher velocities as the magnitude of the data obtained by the processing unit becomes larger than a value nearly equal to the reference velocity, and
  means for displaying together both of the data obtained by the processing unit and an aliasing velocity.

12. The ultrasonic diagnosis apparatus according to claim 3, wherein the processing unit includes means for obtaining the velocities of the moving element within the subject pixel by pixel,
  the displaying unit comprising means for displaying together both of a graph showing temporal changes in the velocities at one or more of the pixels and the image of the data obtained by the processing unit.

13. The ultrasonic diagnosis apparatus according to claim 3, wherein the displaying unit comprises at least one of:
  means for displaying by mixture the image of the data obtained by the processing unit and an information of power information of scattering echoes from the moving element within the subject,
  means for displaying by mixture an image of the power information and an image of information formed by combining the data obtained by the processing unit and the power information,
  means for displaying together both of a color bar for the data obtained by the processing unit and another color bar for the power information,
  means for displaying together both of a color bar indicative of a combination of the data obtained by the processing unit and the power information and another color bar for the power information,
  means for setting an upper limit and a lower limit on the color bar for the data obtained by the processing unit, and
  means for displaying at least one of an upper limit, a lower limit, and an aliasing velocity on the color bar for the data obtained by the processing unit.

14. The ultrasonic diagnosis apparatus according to claim 3, wherein the velocity information is an instantaneous velocity of the velocity data at each pixel, the instantaneous velocity being extracted as a newest one among the velocity data acquired during the predetermined period of time and updated in real time for each pixel.

15. An ultrasonic diagnosis apparatus comprising:
  a scanning unit configured to scan three-dimensionally scanning each of of a subject to be examined a plurality of times during a period of time corresponding to one heartbeat of the subject while transmitting and receiving an ultrasound pulse to and from the subject, whereby reception signals are obtained at each pixel of the section of the subject from the received ultrasound pulse;
  an obtaining unit obtaining, every pixel, velocities of a moving element that is in motion within the subject on the basis of the reception signals obtained during a predetermined period of time based on the one heartbeat of the subject, the velocities being updated in real time;
  a processing unit computing a reference velocity based on the plurality of velocities obtained by the obtaining unit during the predetermined period of time and correcting velocity information based on the velocities of the moving element using the reference velocity, the velocity information indicating a characteristic of the heartbeat of the subject; and
  a displaying unit displaying a three-dimensional image based on the corrected velocity information so that the image in display is updated a plurality of times during the predetermined period of time.

16. The ultrasonic diagnosis apparatus according to claim 15, wherein the scanning unit is configured to three-dimensionally scan the subject through an electrical scan using a two-dimensional array type of transducer, the velocity information is set to a maximum velocity of the velocity data during the predetermined period of time, and the reference velocity is information that is unchangeable over cardiac time phases of the subject.

17. The ultrasonic diagnosis apparatus according to claim 15, wherein the processing unit comprises means for obtaining factors including a pulsatility index (PI) of the object and a resistivity index (RI) of the moving element.

18. The ultrasonic diagnosis apparatus according to claim 15, further comprising a unit obtaining a tomographic image of the sections of the subject, the tomographic image being either of a two-dimensional image or a three-dimensional image,
wherein the display unit has at least one of means for displaying on the same monitor the tomographic image and the image of data obtained by the processing unit and means for displaying on the tomographic image the image of data obtained by the processing unit in a superposition manner.

19. The ultrasonic diagnosis apparatus according to claim 15, wherein the displaying unit comprises at least one of:
means for displaying in colors the image of data obtained by the processing unit,
means for displaying pieces of information formed by combining the data obtained by the processing unit and power information of scattering echoes from the moving element within the subject,
means for displaying a color bar mapped not only by a hue indicative of a lower velocity when magnitudes of the data obtained by the processing unit are nearly equal to or less than the reference velocity but also by other hues indicative of higher velocities as the magnitude of the data obtained by the processing unit becomes larger than a value nearly equal to the reference velocity, and
means for displaying together both of the data obtained by the processing unit and an aliasing velocity.

20. The ultrasonic diagnosis apparatus according to claim 15, wherein the processing unit includes means for obtaining the velocities of the moving element within the subject pixel by pixel,
the displaying unit comprising means for displaying together both of a graph showing temporal changes in the velocities at one or more of the pixels and the image of the data obtained by the processing unit.

21. The ultrasonic diagnosis apparatus according to claim 15, wherein the displaying unit comprises at least one of:
means for displaying by mixture the image of the data obtained by the processing unit and an information of power information of scattering echoes from the moving element within the subject,
means for displaying by mixture an image of the power information and an image of information formed by combining the data obtained by the processing unit and the power information,
means for displaying together both of a color bar for the data obtained by the processing unit and another color bar for the power information,
means for displaying together both of a color bar indicative of a combination of the data obtained by the processing unit and the power information and another color bar for the power information,
means for setting an upper limit and a lower limit on the color bar for the data obtained by the processing unit, and
means for displaying at least one of an upper limit, a lower limit, and an aliasing velocity on the color bar for the data obtained by the processing unit.

* * * * *